United States Patent
Richter et al.

(10) Patent No.: US 9,375,174 B2
(45) Date of Patent: Jun. 28, 2016

(54) ALLOWING MEASUREMENTS TO BE MADE OF A BLOOD SAMPLE

(75) Inventors: Frank Richter, Bad Tölz (DE); Ross MacArthur, Sandbach (GB)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 57 days.

(21) Appl. No.: 13/808,306

(22) PCT Filed: Jul. 7, 2011

(86) PCT No.: PCT/EP2011/061538
§ 371 (c)(1),
(2), (4) Date: Jun. 27, 2013

(87) PCT Pub. No.: WO2012/004356
PCT Pub. Date: Jan. 12, 2012

(65) Prior Publication Data
US 2013/0274579 A1    Oct. 17, 2013

(30) Foreign Application Priority Data
Jul. 8, 2010 (EP) .................................. 10168956

(51) Int. Cl.
*A61B 5/00* (2006.01)
*A61B 5/151* (2006.01)
*A61B 5/15* (2006.01)

(52) U.S. Cl.
CPC ........... *A61B 5/15103* (2013.01); *A61B 5/1411* (2013.01); *A61B 5/15146* (2013.01); *A61B 5/15186* (2013.01)

(58) Field of Classification Search
CPC .......... A61B 5/14; A61B 5/1411; A61B 5/15; A61B 5/151; A61B 5/15107; A61B 5/15115; A61B 5/15117; A61B 5/15126; A61B 5/15128; A61B 5/15146; A61B 5/15148; A61B 5/15151; A61B 5/151525; A61B 5/15159

USPC .................................. 600/583; 606/181–183
See application file for complete search history.

(56) References Cited

U.S. PATENT DOCUMENTS 5,201,324 A * 4/1993 Swierczek .................... 600/583
6,802,199 B2 * 10/2004 Hilgers et al. ............... 72/370.1
(Continued)

FOREIGN PATENT DOCUMENTS

EP 1880671 1/2008
EP 2042098 4/2009
(Continued)

OTHER PUBLICATIONS

International Search Report for Int. App. No. PCT/EP2011/061538, completed Aug. 19, 2011.
(Continued)

*Primary Examiner* — Max Hindenburg
(74) *Attorney, Agent, or Firm* — McDonnell Boehnen Hulbert & Berghoff LLP

(57) ABSTRACT

An apparatus and a method for measuring a property of a blood sample is shown. The apparatus comprises of a housing having an aperture; a shaft mounted inside the housing; a testing member rotatably mounted on the shaft; an actuating member coupled to the housing and configured to exert a force against the testing member; and a lancet for eliciting a blood sample fixedly coupled to and protruding substantially radially from the testing member and configured to co-rotate with the testing member. The apparatus is further configured such that the lancet is aligned with the aperture in the housing when the testing member is in a first position. The testing member is configured, in the presence of a force exerted against the testing member by the actuator member, to translate to a second position in which the lancet is in a skin penetrating position.

12 Claims, 22 Drawing Sheets

(56) References Cited

U.S. PATENT DOCUMENTS

| | | | | |
|---|---|---|---|---|
| 7,150,755 | B2* | 12/2006 | Levaughn | A61B 5/1411 600/583 |
| 7,175,642 | B2* | 2/2007 | Briggs | A61B 5/1411 600/583 |
| 7,998,161 | B2* | 8/2011 | Shi | A61B 5/15142 606/182 |
| 8,231,548 | B2* | 7/2012 | Hoenes | 600/583 |
| 8,394,035 | B2* | 3/2013 | Haar et al. | 600/583 |
| 8,506,505 | B2* | 8/2013 | Hoenes | 600/583 |
| 8,870,903 | B2* | 10/2014 | LeVaughn | A61B 5/1411 604/218 |
| 8,961,431 | B2* | 2/2015 | Roe | A61B 5/1411 600/583 |

FOREIGN PATENT DOCUMENTS

| | | |
|---|---|---|
| WO | 2005/018425 | 3/2005 |
| WO | 2009/116312 | 9/2009 |

OTHER PUBLICATIONS

International Preliminary Report on Patentability for Int. App. No. PCT/EP2011/061538, mailed Jan. 17, 2013.

* cited by examiner

ALLOWING MEASUREMENTS TO BE MADE OF A BLOOD SAMPLE

CROSS REFERENCE TO RELATED APPLICATIONS

The present application is a U.S. National Phase Application pursuant to 35 U.S.C. §371 of International Application No. PCT/EP2011/061538 filed Jul. 7, 2011, which claims priority to European Patent Application No. 10168956.0 filed on Jul. 8, 2010. The entire disclosure contents of these applications are herewith incorporated by reference into the present application.

FIELD OF INVENTION

This invention relates to apparatus and method for allowing measurements to be made of a blood sample. The invention relates also to apparatus comprising a blood analysis part for receiving a blood sample.

BACKGROUND

Diabetes sufferers may be provided with quantities of insulin, for instance by injection, sometimes a number of times daily. The quantity of insulin that is appropriate depends on the person's blood glucose level, so blood glucose level measurement can also occur a number of times daily.

Blood glucose level measurement typically is a multi stage process. The first is lancing, in which a lancet, or needle, is used to pierce the skin of a user, for example on the end or side of a finger. Once a suitable amount of blood has been produced, a sample is taken on a testing strip. A person may need to squeeze their finger in order to cause sufficient blood to be expelled. Sometimes lancing needs to be reperformed. The testing strip then is provided to a meter, typically an electronic meter, which analyses the sample, for example by determining a parameter (e.g. an electrochemical potential or voltage, resulting from a chemical reaction between the blood sample and an enzyme present in the testing strip, and provides a blood glucose measurement result. This measurement is then used to determine an amount of insulin to be consumed by the person.

Lancing can be painful or at least uncomfortable for a user. Numerous efforts have been made to reduce or minimise discomfort to a user in the lancing process. More effective efforts typically involve more complicated, and thus more expensive, mechanical or electro-mechanical arrangements.

SUMMARY

According to a first aspect of the invention there is provided apparatus for eliciting a blood sample, the apparatus comprising:
  a housing having an aperture;
  a shaft mounted inside the housing;
  a testing member rotatably mounted on the shaft;
  an actuating member coupled to the housing and configured to exert a force against the testing member; and
  a lancet fixedly coupled to and protruding substantially radially from the testing member and configured to co-rotate with the testing member;
  wherein the apparatus is configured such that the lancet is aligned with the aperture in the housing when the testing member is in a first position, and
  wherein the testing member is configured, in the presence of a force exerted against the testing member by the actuator member, to translate to a second position in which the lancet is in a skin penetrating position.

This can allow particularly effective lancing to be achieved whilst allowing the advantages that can be experienced by use of a testing member that is rotatably mounted on a shaft.

The testing member may further comprise a blood sample collection part. Such a combined lancing and blood collection apparatus can reduce the number of actions needed by a user to perform a blood parameter measurement, such as a blood glucose measurement.

According to a second aspect of the invention there is provided a method of eliciting a blood sample, the method comprising:
  rotating a testing member on a shaft mounted inside a housing to a first position so as to align a lancet protruding substantially radially from the testing member with an aperture in the housing, and
  an actuator member exerting a force against the testing member to translate the testing member to a second position in which the lancet is in a skin penetrating position.

BRIEF DESCRIPTION OF THE DRAWINGS

Embodiments of the invention will now be described, by way of example only, with reference to the accompanying drawings, in which.

DETAILED DESCRIPTION

Figure 1:
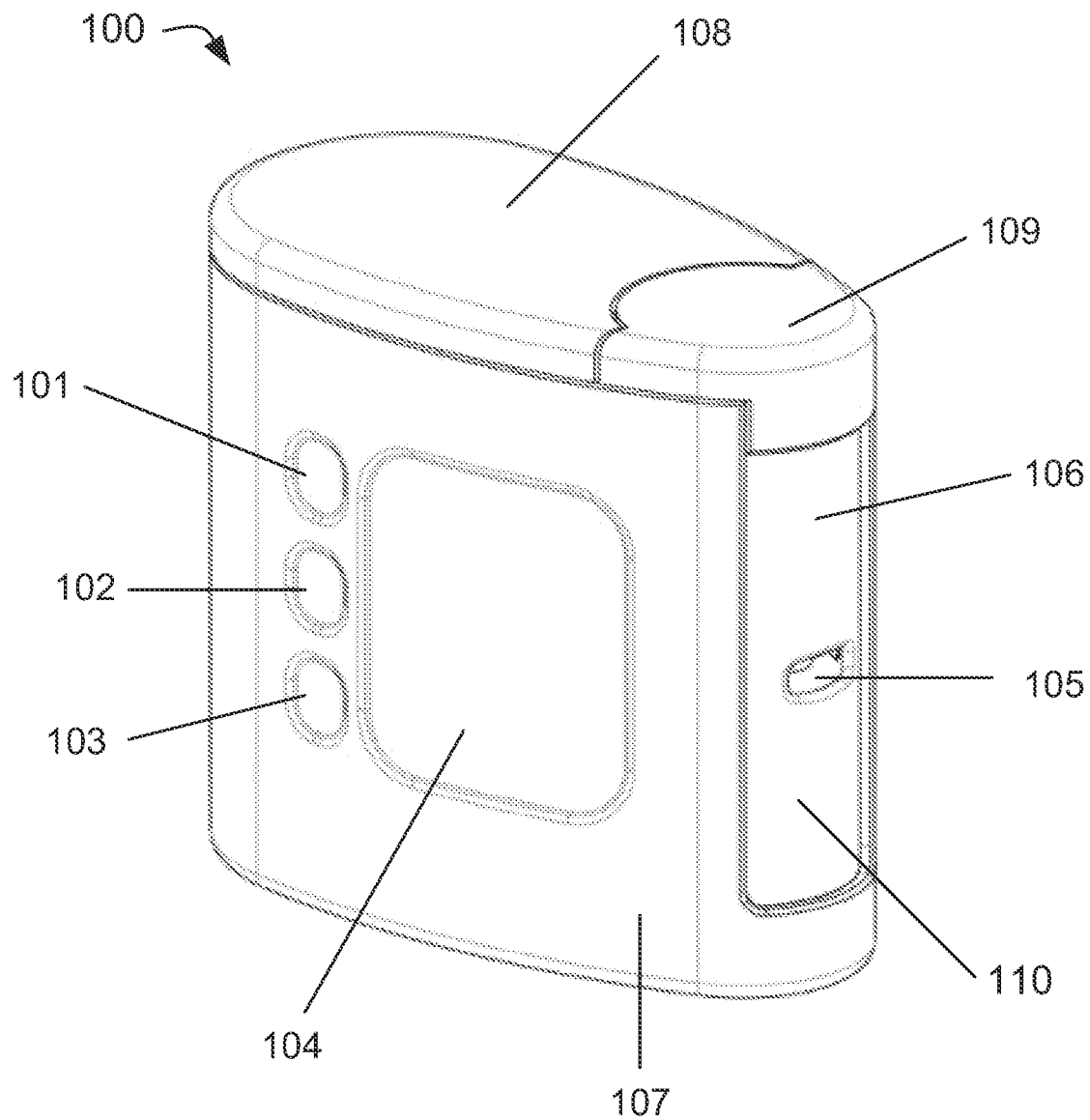
FIG. 1 is a perspective view of a blood glucose meter (BGM) according to aspects of the invention.

A blood glucose meter (BGM) 100 is shown in FIG. 1. The BGM 100 is shown in a perspective view. The BGM 100 has a generally flat base, that is not visible in the figure. The BGM 100 is approximately as tall as it is long, and its width is approximately one-third of its height On one side face of the BGM are provided first, second and third inputs 101, 102, 103. These may take the form of push-switches or touch sensitive transducers, for instance. Also provided on the side of the BGM next to the input devices 101 to 103 is a display 104. This may take any suitable form, for instance a liquid crystal display (LCD), e-ink etc. In use, a user may control the BGM 100 using the input devices 101 to 103 and may be provided with information by the BGM through the display 104.

Located at a front face of the BGM 100 is an aperture 105. The aperture 105 is located at approximately half of the height of the BGM. The aperture 105 is configured such as to be able to receive a part of a user's body, for the purpose of extracting a blood sample therefrom. For instance, the aperture 105 may be dimensioned so as to receive an end or a side part of a finger or thumb, or may be dimensioned so as to receive a side of a user's hand or a pinch of skin from a user's arm. The aperture may be rectangular in shape. Its edges may be bevelled, so as to guide a user's digit into a specific location.

The aperture 105 is provided in the side of a cartridge 106. The cartridge has a generally cylindrical form, and is arranged vertically in the BGM 100.

In particular, the BGM includes a first housing part 107. The first housing part 107 forms the base, left and right side face and the rear face of the BGM 100. On the front face of the BGM 100, the first housing part 107 also comprises the lowermost part of the side face. A fixed lid part 108 is attached to the first housing part 107. The fixed lid part 108 comprises most of the top surface of the BGM 100. A removable lid part 109 comprises the remaining part of the top surface of the BGM 100. The removable lid part is disposed above the cartridge 106 at the front face of the BGM 100.

The first housing part 107 is configured such as to provide an elongate aperture 110 at the front face of the BGM 100. The elongate aperture 110 may extend for most of the height of the front face of the BGM 100. The elongate aperture 110 is defined at the uppermost part by the removable lid part 109 and is defined by the first housing part 107 at the right, left and bottom. The BGM 100 is arranged such that the cartridge 106 occupies the whole of the area of the elongate aperture 110. A slidable or pivotable door in the housing part 107 of the BGM 100 may cover all or a part of the elongate aperture 110 when the BGM is not in use. The door may cover at least the aperture 105, such as to prevent the ingress of dirt and other potential contaminants into the aperture 105

Figure 2:
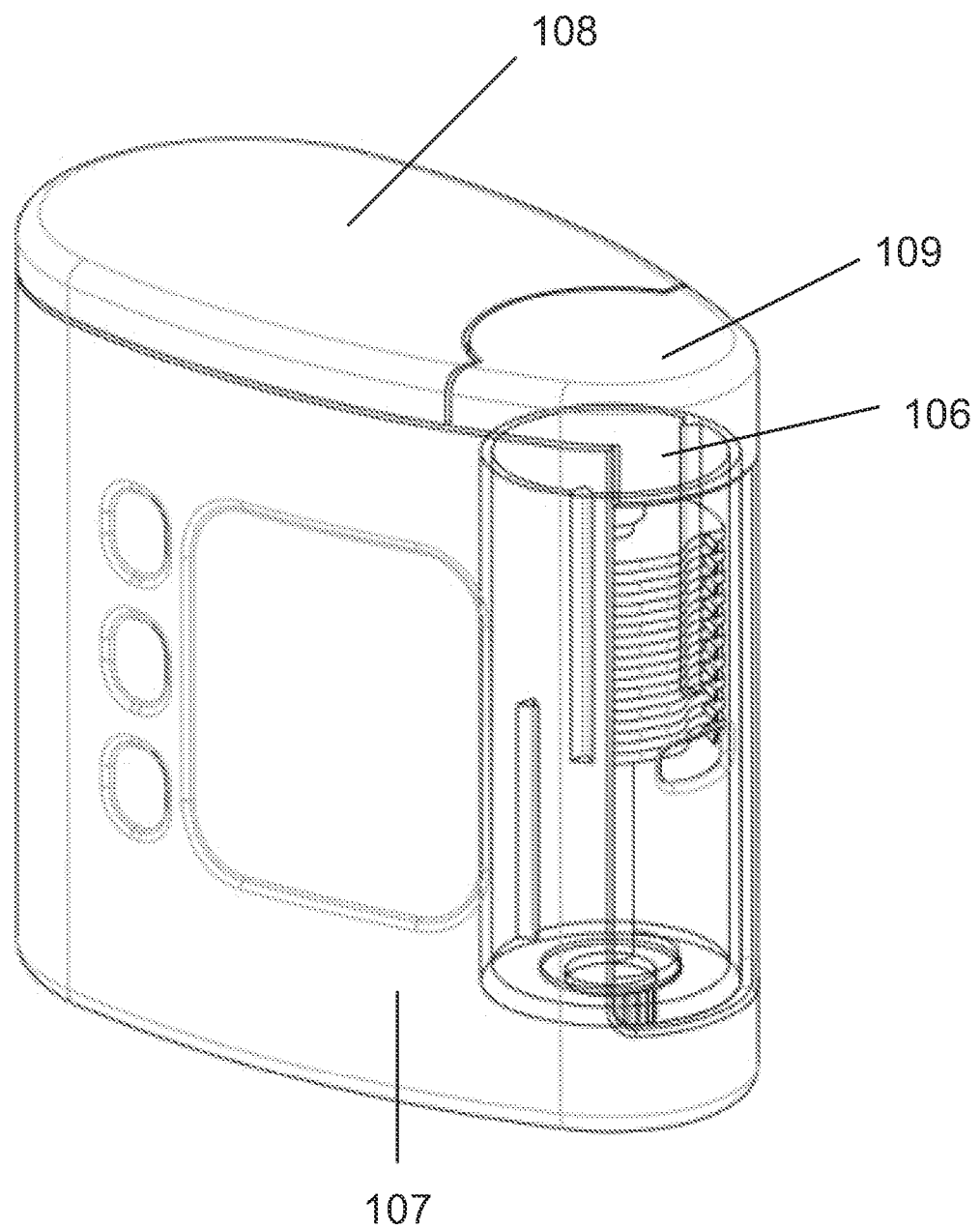
FIG. 2 is a perspective view of the BGM of FIG. 1 with a portion shown as transparent, so as to allow features inside a housing to be seen.

The cartridge 106 is more clearly visible in FIG. 2. FIG. 2 shows the same view as FIG. 1, although the removable lid part 109 and the first housing part 107 are shown in wire frame. As can be seen from FIG. 2, the cartridge 106 has a generally cylindrical form, and is arranged vertically. The diameter of the cartridge 106 is greater than the width of the aperture 110 by a factor for instance of between 5 and 50%. The cartridge 106 has a length that is between 3 or 4 times its diameter.

Figure 3:
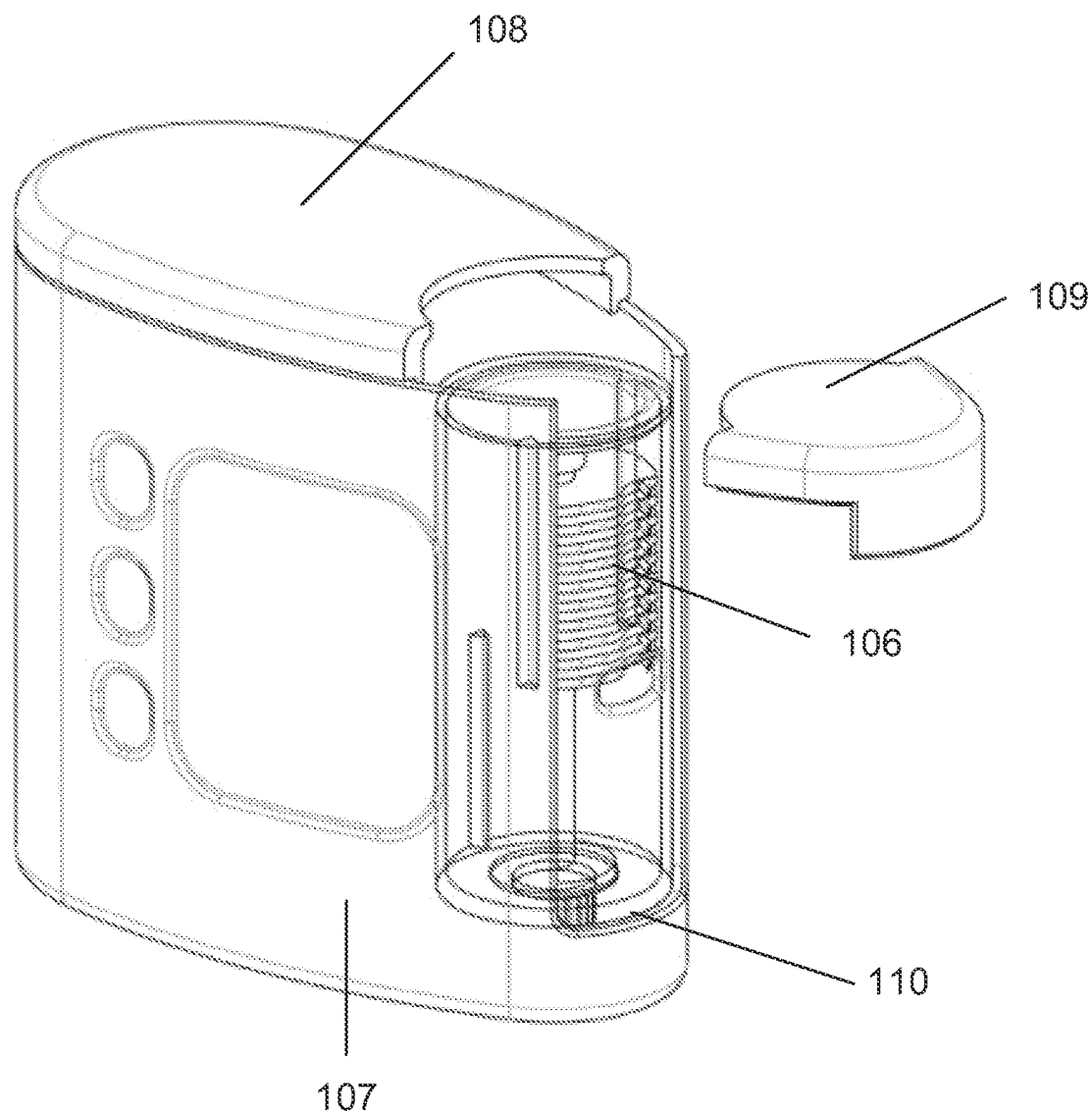
FIG. 3 is the same as FIG. 2 although a lid portion is shown as being removed.

In FIG. 3, the removable lid part 109 is shown as having been removed from the BGM 100. The first housing part 107, the fixed lid part 108 and the removable lid part 109 are configured such that when the removable lid part is in place on the BGM the cartridge 106 is retained by mechanical interaction between the three components but is removable by a user. The exact way in which the removable lid part 109 is released from the BGM 100 is not critical and is not described in detail here.

Figure 4:
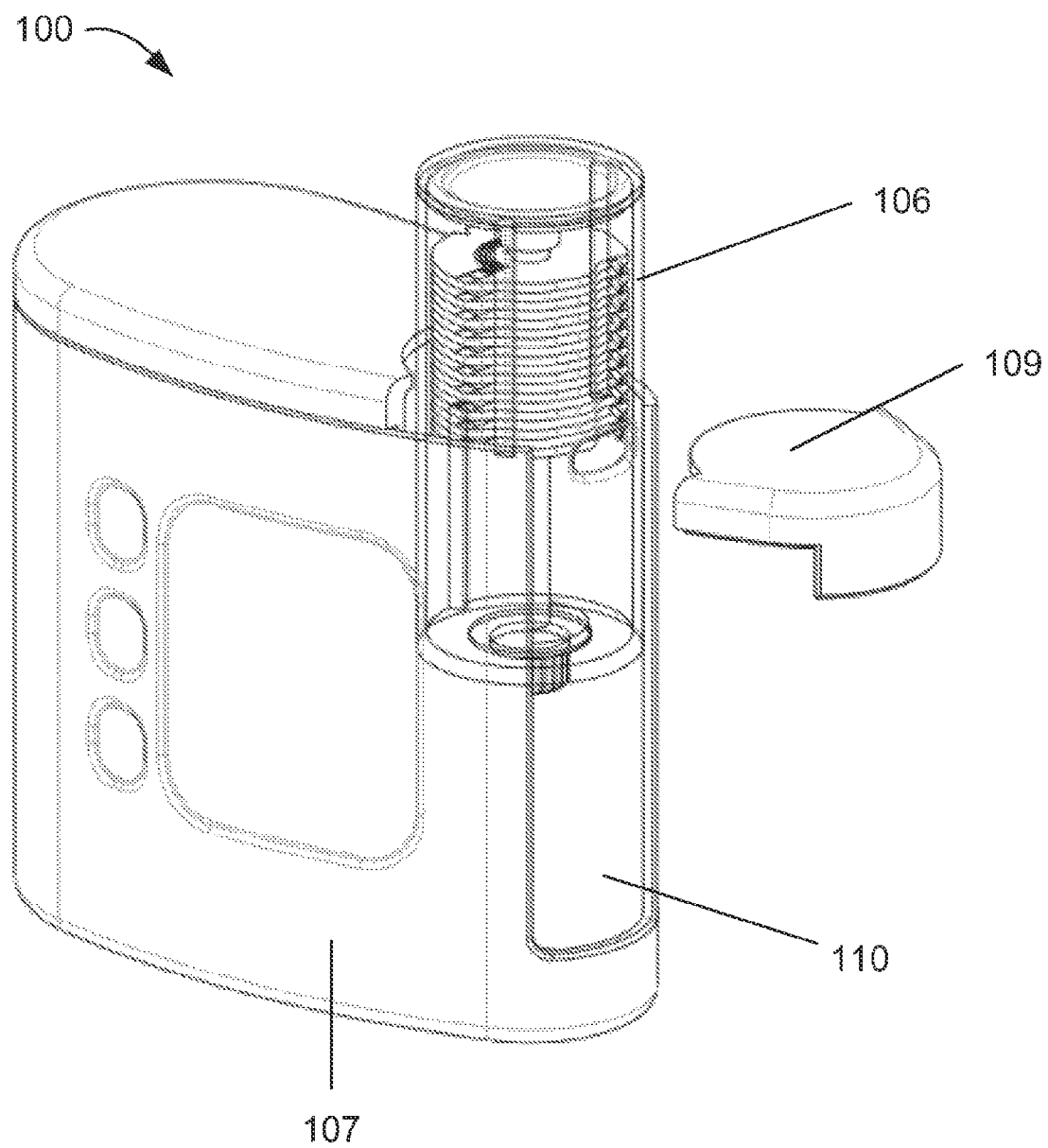
FIG. 4 is the same as FIG. 3, although a cartridge is shown as partly removed.

The removable lid part 109 is configured such that when removed from the BGM 100 the cartridge 106 is able to be extracted from the BGM by moving it vertically along its axis. In FIG. 4, the cartridge 106 is shown as being partly removed from the BGM 100. When fully removed, the elongate aperture 110 reveals a cavity in the BGM 100. A replacement cartridge can then be introduced into the BGM 100 in the opposite manner to which the old cartridge 106 was removed. Once located at the bottom of the cavity in the BGM, the new cartridge 106 is partly surrounded by the first housing part 107. Once the removable lid part 109 has been replaced, to the position shown in FIG. 1, the cartridge 106 is retained in place by the action of the first housing part 107 and the removable lid part 109. The aperture 105 in the cartridge 106 is presented at the front face of the BGM 100, in the same way as shown in FIG. 1. The cartridge 106 and the cavity which receives the cartridge may have a keying feature, such as a protrusion and a groove, a non circular diameter, or the like. Thus, when the cartridge 106 is fully inserted, the aperture 105 is in a fixed position to the elongate aperture 110, for example in a centred position as shown in FIG. 1.

Figure 5:
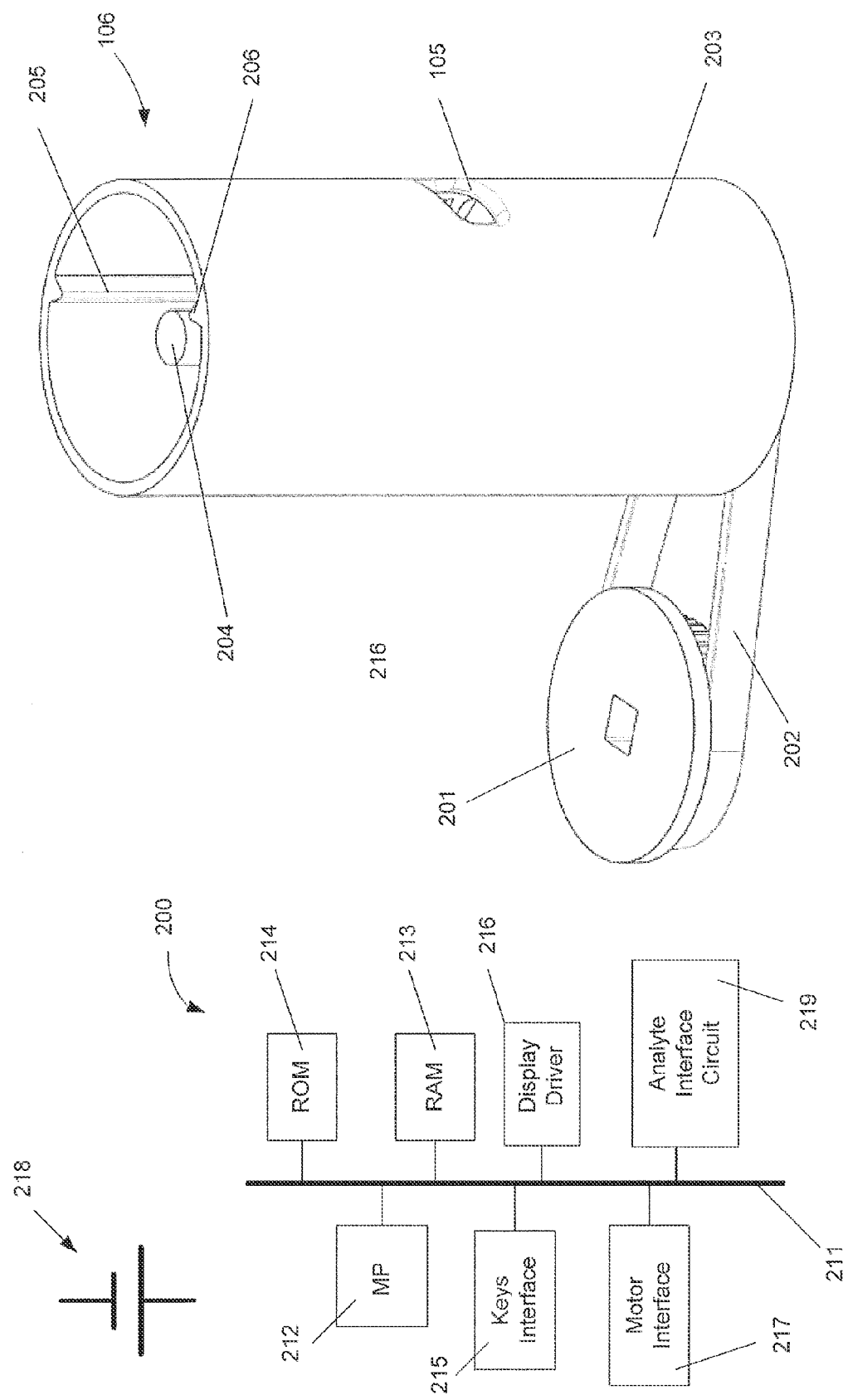
FIG. 5 illustrates components of a BGM that is outside the scope of the claims but includes features of embodiments of the invention.

FIG. 5 shows a subsystem 200 of the blood glucose meter 100. The subsystem 200 includes the cartridge 106, a drive wheel 201 and a drive belt 202.

In FIG. 5, the cartridge shown as having a hollow cylindrical housing part 203, which constitutes part of a housing. The aperture 105 is formed in the hollow cylindrical housing part 203. Coaxial with the hollow cylindrical part 203 is an elongate shaft 204, only the top part of which is illustrated in FIG. 5. The length of the shaft 204 is such that its uppermost end is slightly below the uppermost end of the hollow cylindrical housing part 203. As will be described below, the shaft 204 is mechanically coupled with the drive belt 202 so as to be rotatable by rotation of the drive wheel 201.

Formed with the inner surface of the hollow cylindrical housing part 203 are first and second guide members 205, 206. In FIG. 5, it can be seen that the first and second guide members 205, 206 have a generally triangular cross section. One side of the triangular cross section of the first and second guide members 205, 206 is integral with the inner surface of the hollow cylindrical housing part 203, with a point of the triangular cross section extending towards the centre of the cartridge 106. A part of the length of the first guide member 205 is visible in FIG. 5, but only the uppermost surface of the second guide member 206 is visible in that figure.

FIG. 5 also shows some electronic components that form parts of the blood glucose meter 100. These components are provided within the housing 107 but do not form part of the cartridge 106.

A bus 211 is arranged to connect a number of components including a microprocessor 212, random access memory (RAM) 213, read-only memory (ROM) 214, a keys interface 215, a display driver 216, an analyte interface circuit 219 and a motor interface 217. All of these components are powered by a battery 218, which may take any suitable form.

Stored in the ROM 214 is software and firmware that governs operation of the blood glucose meter 100. The software/firmware is executed by the microprocessor 212 using the RAM 213. The software/firmware stored in the ROM 214 is operable to operate the blood glucose meter 100 such as to allow control by a user through the keys or input devices 101 to 103, as detected by the keys interface 215. A blood glucose measurement and other information is provided on the display 104 at suitable times by operation of the software/firmware and the microprocessor 212 through the display driver 216.

The motor interface 217 allows the microprocessor 212, according to the software/firmware stored in the ROM 214, to control the motor that is coupled to the drive wheel 201, and any other motors that are included in the blood glucose meter 100 (as will be described below).

The analyte interface circuit 219 is operable to provide electrical signals with certain voltages to the electrical contact terminals 401, and thus the contact pads 318 and thus the analyte measuring part 316, and to measure parameters of signals such as to allow the microprocessor 212 to determine a blood glucose level of a blood sample.

FIGS. 6 to 12 are outside the scope of the claims but provide useful e4planation of some features of embodiments of the invention.

Figure 6:
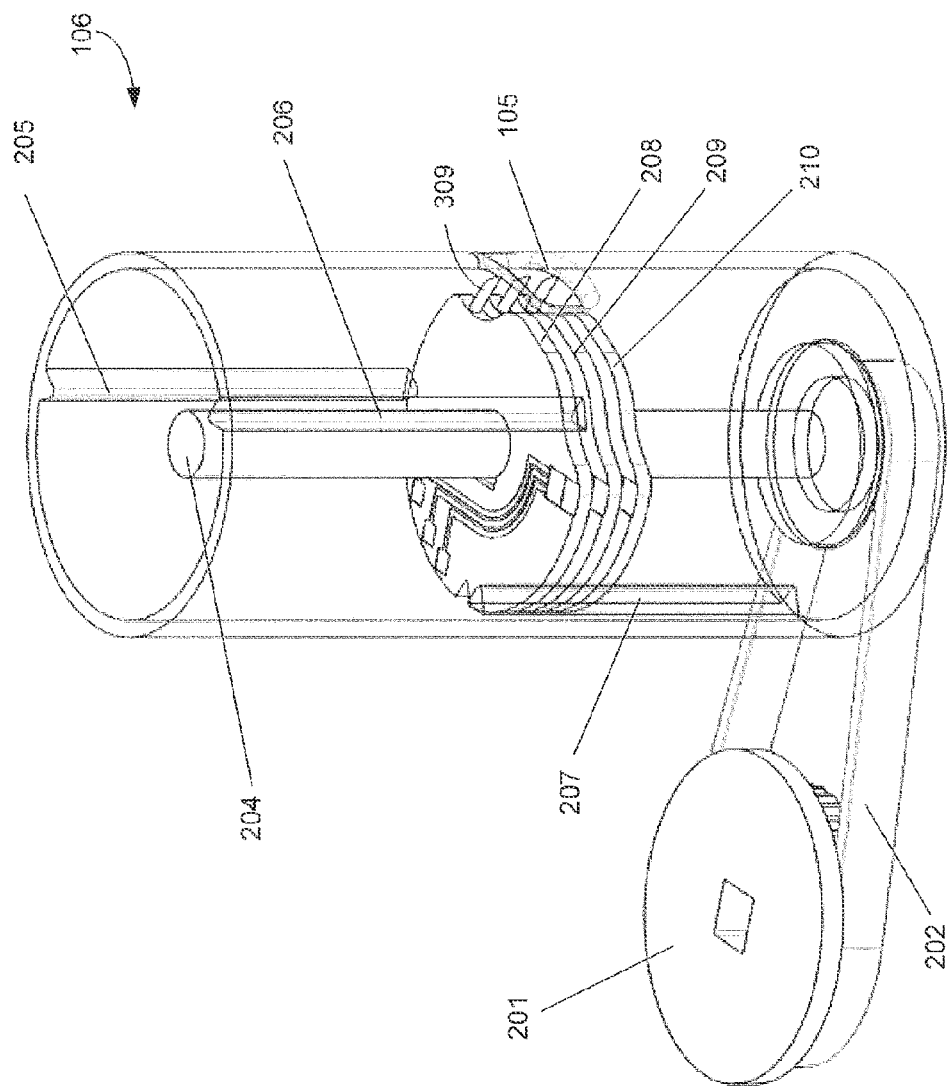
FIG. 6 is a perspective view of components of the BGM of FIG. 5 but with a hollow cylindrical housing part shown as transparent.

FIG. 6 shows the drive wheel 201 and cartridge 106 of FIG. 5 with the hollow cylindrical housing part 203 shown in wire frame, so as to reveal components internal to it, and in that the electronic components are omitted. In FIG. 6, a third guide member 207 is visible. As can be seen from this figure, the first and second guide members 205, 206 are located only in the uppermost half of the length of the cartridge 106, and the third guide member 207 is located only in the lowermost half of the cartridge 106. The first, second and third guide members 205 to 207 are distributed around the circumference of the hollow cylindrical housing part 203. In particular, the first and second guide members 205, 206 are located at approximately 100 to 160 degrees from one another. The third guide member 207 is located approximately 60 to 130 degrees from each of the first and second guide members 205, 206.

Mounted on the shaft 204 are a plurality of members, three of which are shown in FIG. 6 as 208, 209 and 210 respectively. The members 208 to 210 will hereafter be referred to as test disc members. Each of the test disc members 208 to 210 is substantially the same.

Figure 7:
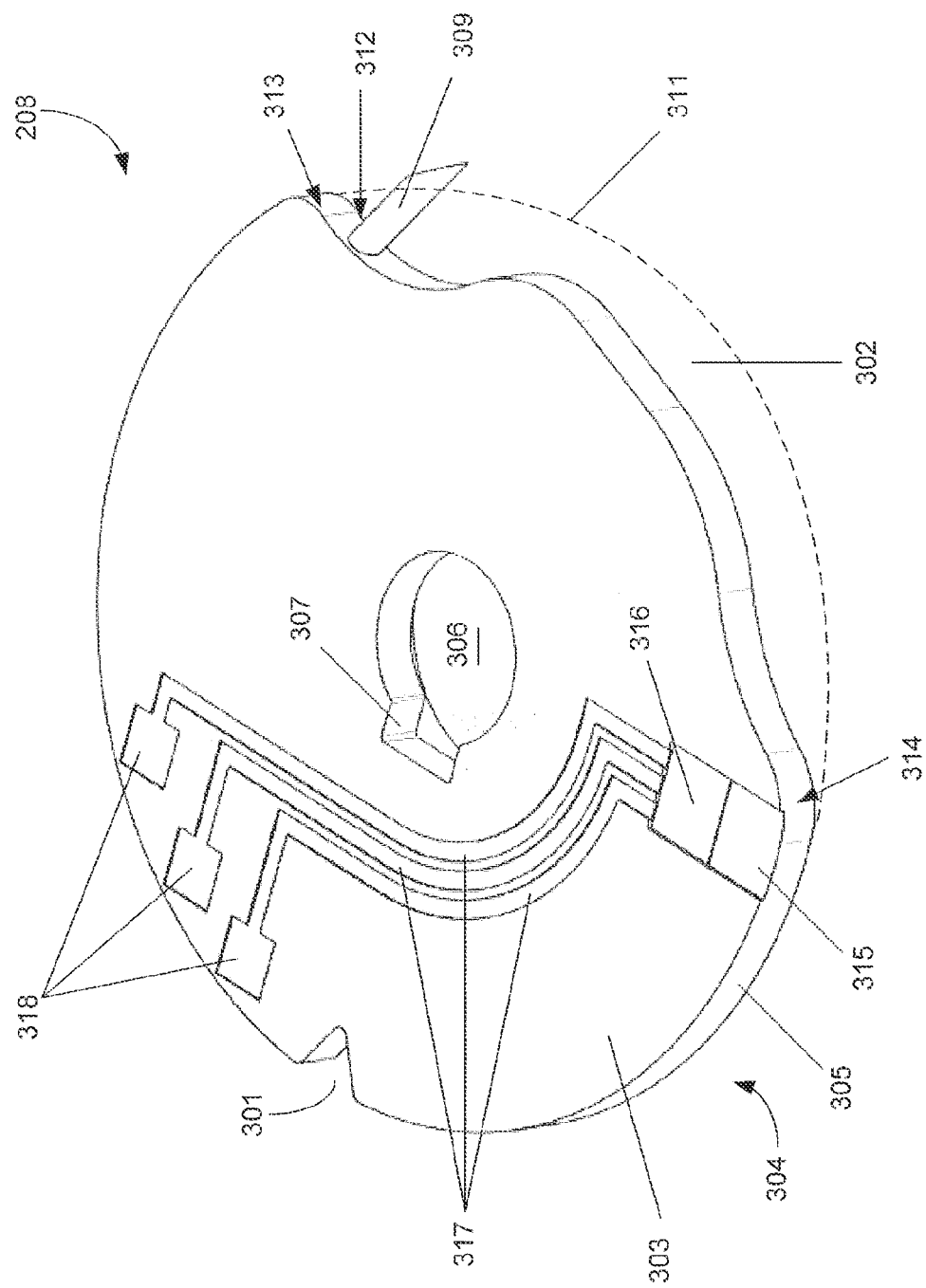
FIG. 7 is a perspective view of a test disc member forming part of the BGM of FIGS. 1 and 5.

One test disc member 208 is shown in some detail in FIG. 7. The test disc member 208 has a generally circular shape, although on one side a notch 301 is formed and on another side a cutaway portion 302 is provided. The cutaway portion 302 constitutes a milking portion.

Figure 8:
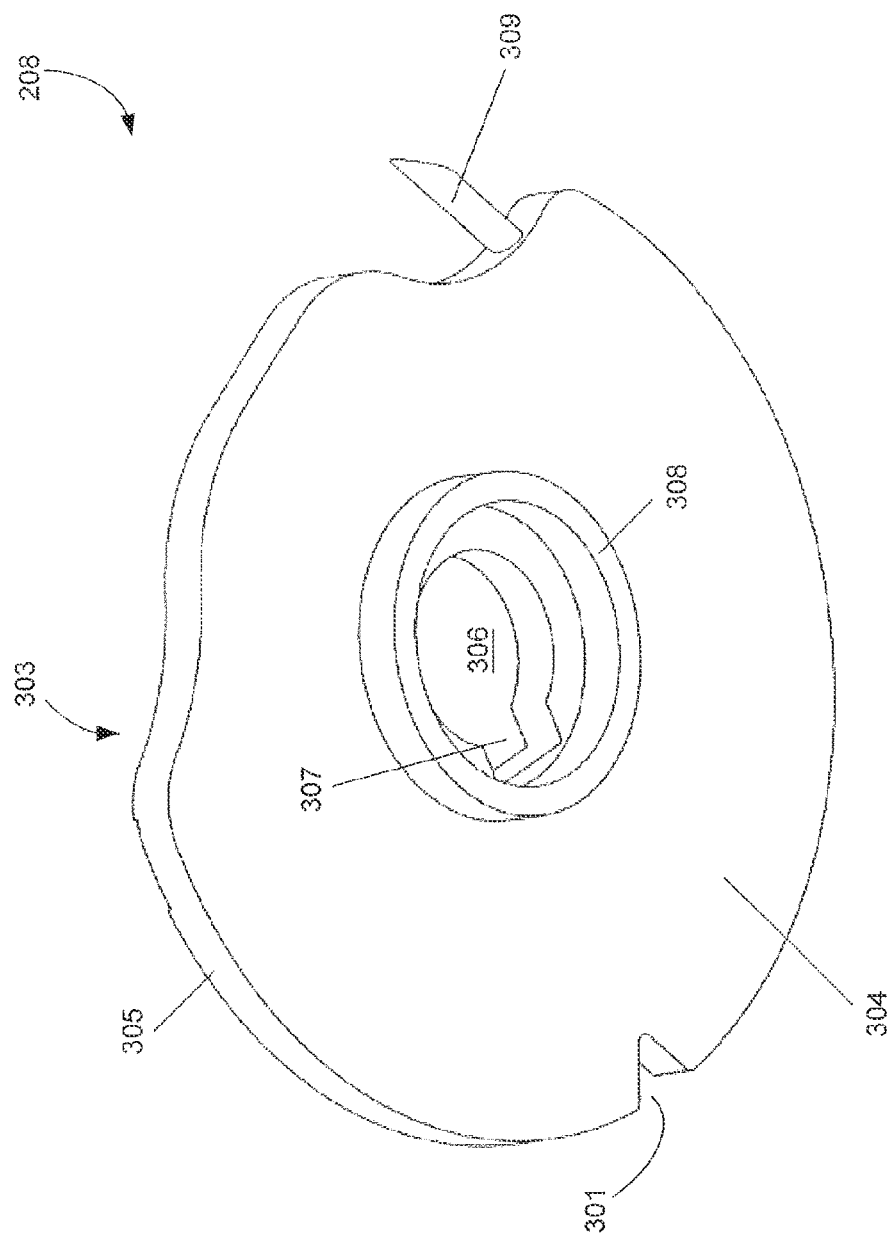
FIG. 8 is an underneath perspective view of the test disc member of FIG. 7.

The test disc member 208 includes an uppermost surface 303, a lowermost surface 304, which is shown in FIG. 8, and a disc edge 305. The diameter of the test disc member 208 is between 15 and 25 millimeters, for instance 20 millimeters. The thickness of the disc, which is equal to the height of the disc edge 305, is between 0.5 millimeters and 1 millimeter. FIG. 8 shows the test disc member 208 from the underside. As such, the lower surface 304 is visible and the upper surface 303 is not visible. The test disc member 208 will now be described with reference to FIGS. 7 and 8.

A hole 306 is formed at the centre of the test disc member 208. The hole 306 comprises two main parts. A circular part is centred on the test disc member 208 and has a diameter equal to or slightly larger than the external diameter of the shaft 204. A drive notch 307 abuts the circular part of the hole 306 and includes edges that are able to be engaged by a drive dog.

A drive dog 320 (visible in part in FIG. 9 and more fully in FIG. 10) is formed on the shaft 204. The drive dog 320 is engaged with the drive notch 307 in the hole 306 of the test disc member 208. This engagement allows rotation of the shaft 204 to result in rotation of the test disc member 208.

On the underside of the test disc member 208 is provided a spacer member 308. The spacer member 308 comprises a slice of a hollow cylinder. The cylinder is centred on the centre of the test disc member 208. The inner diameter of the spacer member 308 is selected such that the hole 306 does not overlap with the spacer member 308. The outer diameter of the spacer member 308 is only slightly greater than the inner diameter, so the spacer member 308 has little thickness. The height of the spacer member 308 is between 0.5 and 1 millimeter. When plural test disc members are stacked together, the spacer member 308 provides separation between the upper surface 303 of one test disc member and the lower surface 304 of the test disc member that is directly above it. The separation is determined by the height of the spacer member 308.

Referring again to FIG. 7, a lancet 309 is shown protruding from the disc edge 305. The lancet 309 is provided in the cutaway portion 302. A first end of the lancet 309 is embedded within the material of the test disc member 208, and a second end is provided with a sharp point and extends outwardly. The lancet 309 extends at an angle between 30 and 60 degrees from a radius line of the test disc member 208 at the position where the end of the lancet 309 is embedded in the test disc member. The second end of the lancet 309 is located at or just outside a circumference 311 of the test disc member 208. The circumference 311 is shown as a dotted line in FIG. 7 because it is virtual, instead of tangible. The lancet 309 extends from the disc edge 305 at a first position 312 on the disc edge. The first position 312 is close to a second position 313 at which the cutaway portion 302 starts. The cutaway portion 302 ends at a third position 314. Between the second and third positions 313, 314 opposite to the cutaway portion 302, the disc edge 305 generally takes the form of a circle, although the notch 301 interrupts that circle.

Located next to the third position 314 is a blood collection part 315. This may take any suitable form. For instance, it may comprise a laminated material. The blood collection portion 315 has the function of drawing blood that is in contact with the disc edge 305 at the third position into the test disc member 208 to an blood analyte measuring part 316, that adjoins the blood collection part 315, for example a part containing an enzyme for blood glucose measuring, or the like. Blood may be drawn through capillary action. The analyte measuring part 316 includes an enzyme that reacts chemically with blood in such a way that blood glucose level can be measured. The analyte measuring part 316 is connected to first to third contact pads 318 by first to third conductive tracks 317. The contact pads 318 and the conductive tracks 317 are formed on the upper surface 303 of the test disc member 208. The analyte measuring part 316 analyte measuring part 316 also is formed on the upper surface 303 of the test disc member 208. Some or all of the conductive tracks 317, the contact pads 318 and the analyte measuring part 316 may be printed onto the upper surface 303 of the test disc member 208. In an alternative embodiment, the test disc member 208 may have only 2 contact pads. In yet another embodiment, the test disc member 208 may have more than 3 contact pads, for example, 4 or 5 contact pads.

In use a part of a user is firstly pierced by the lancet 309, the part is then milked by the disc edge 305 at the cutaway portion 302, and blood then is provided to the analyte measuring part 316 through the blood collecting portion 315. A measuring circuit connected to the analyte measuring part 316 by way of the conductive tracks 317 and the contact pads 318 then is able to determine a blood glucose level of the user. The level then is displayed on the display 104.

Operation will now be described with reference to the figures.

As shown in FIG. 6, the test disc members 208 to 210 commence at the same orientation. Here, the first test disc member 208 is uppermost. The third guide member 207 is located in the notch 301 of the lowermost test disc members 209, 210. The notch 301 of the first test disc member 208 is aligned with the third guide member 207, but is not constrained thereby. The upper surface 303 of the uppermost test disc member 208 is in contact with a lowermost surface of the first guide member 205. The lowermost surface of the second guide member 206 is at the same level as the lowermost end of the first guide member 205. However, the second guide member 206 coincides with part of the cutaway portion 302 of the first test disc member 208 at the orientation of the test disc member 208 shown in FIG. 6. As such, there is no contact between the second guide member 206 and the first test disc member 208 when the first test disc member is in this position. The test disc members 208 to 210 are biased in an upwards direction by bias means (not shown), which may be a spring. However, the test disc members 208 to 210 are prevented from moving upwards within the cartridge 106 by virtue of the contact between the upper surface 303 of the first test member 208 and the lowermost end of the first guide member 205.

At the position shown in FIG. 6, the distal end of the lancet 309 is not co-located with the aperture 105. As such, the lancet 309 is in this position not operational. Put another way, the lancet 309 at this position is shielded by the hollow cylindrical part 203, which constitutes part of the housing.

Figure 9:
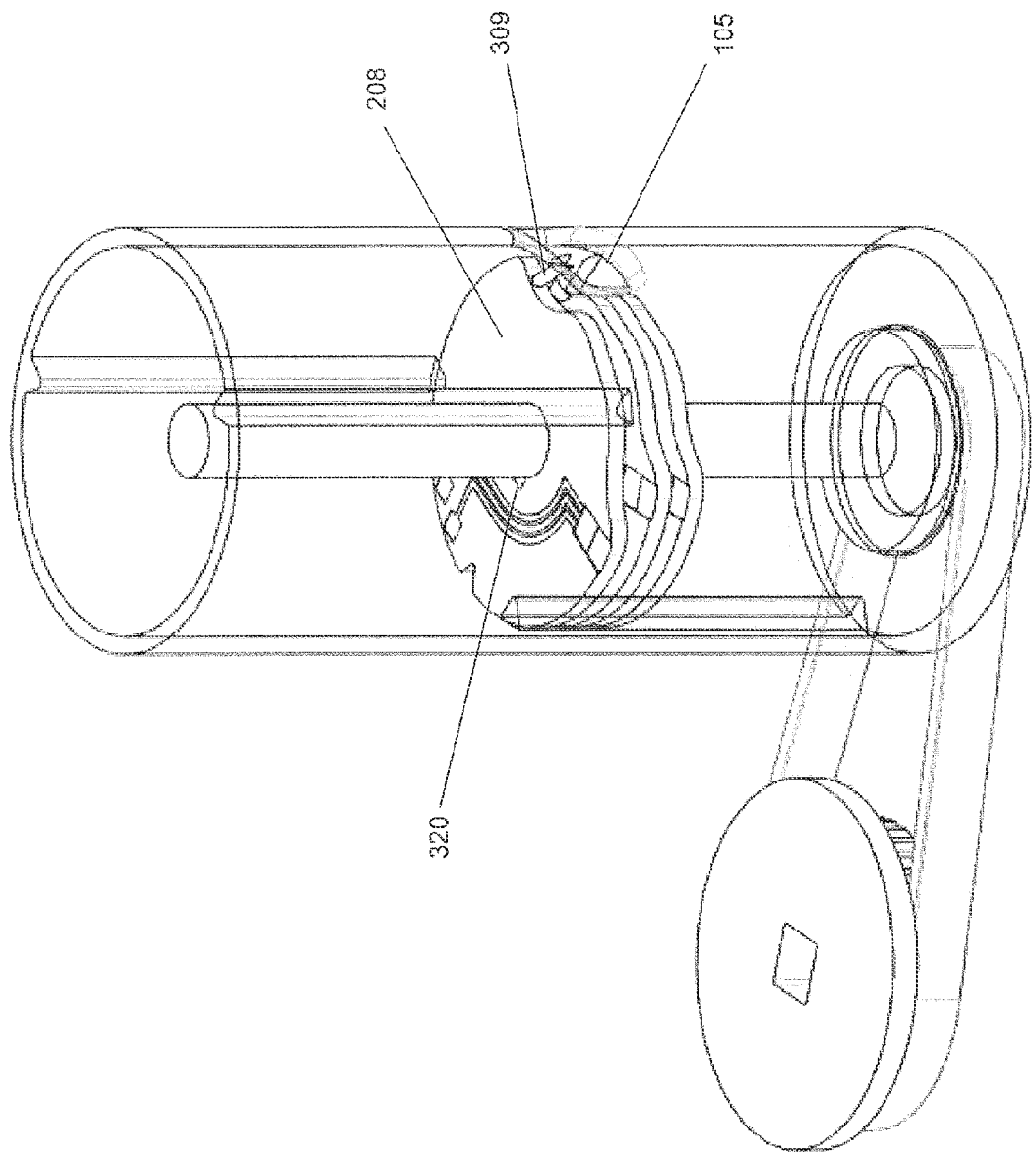
FIGS. 9 to 12 illustrate the BGM of FIGS. 5 to 7 at different stages of a blood collection sample process.
Figure 10:
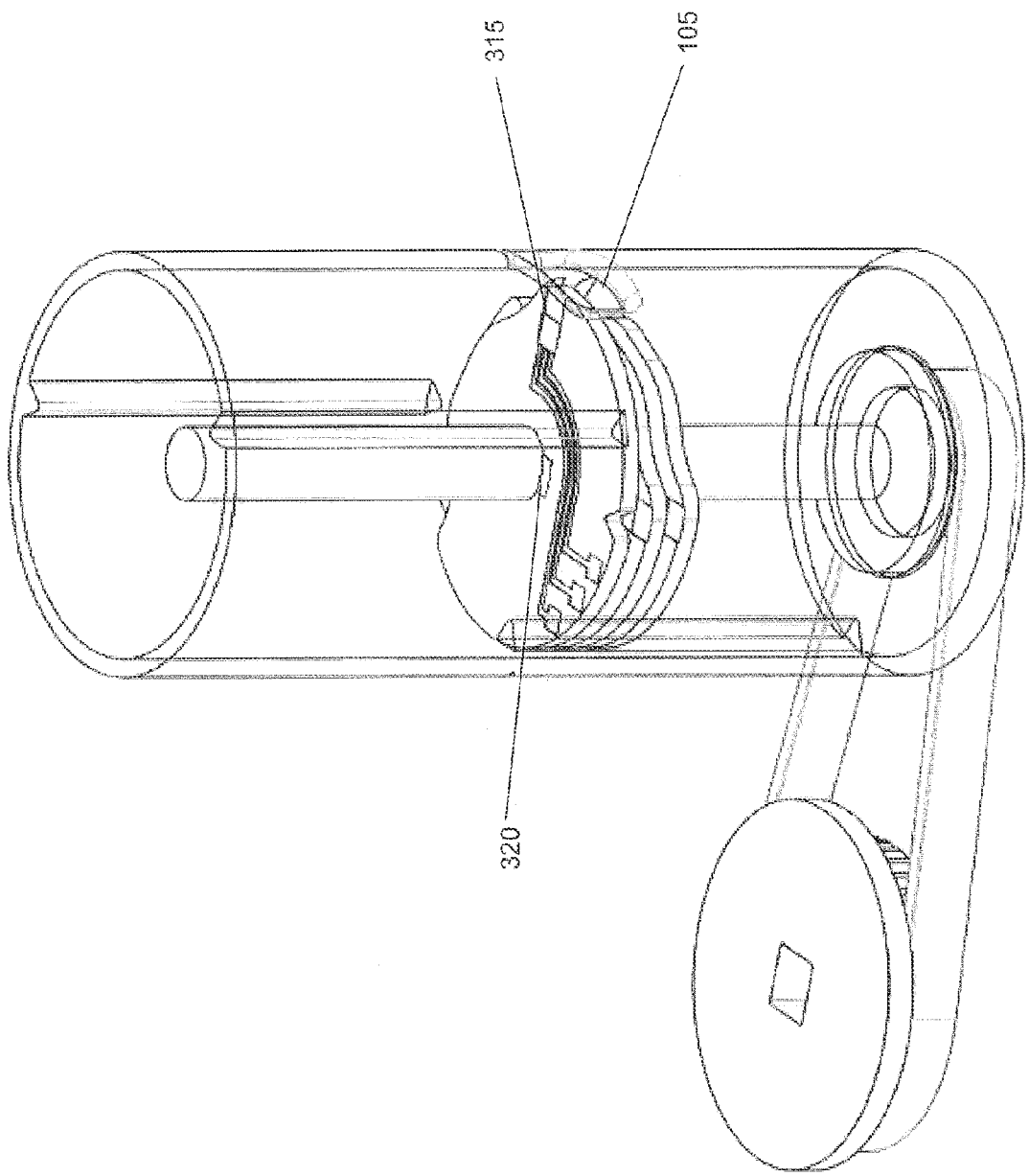

From the position shown in FIG. 6, the shaft 204 is caused to rotate in a first direction, for example in a clockwise direction, by action of the drive wheel 201 and drive belt 202. The drive dog 320 is engaged with the drive notch 307 in the hole 306 of the test disc member 208, and so allows rotation of the shaft 204 to result in rotation of the test disc member 208. Rotation brings the lancet 309 in front of the aperture 105. As such, a skin-covered part of a user (hereafter the part will be referred to as a user's digit, for the sake of convenience) is lanced by the lancet 309. This produces a puncture in the skin of the digit, through which blood can escape. FIG. 9 shows the first test disc member 208 rotated to the position where the lancet 309 is operable to lance the user's digit. The shaft 204 is caused to rotate only by a predetermined amount, the maximum extent of travel of the lancet 309 is controlled. The penetration of the lancet 309 in the user's digit depends on a number of factors, as will be appreciated by the person skilled in the art. The amount of rotation, and thus the depth of penetration, may be definable by a user.

Subsequently, the shaft 204 is controlled to rotate in an opposite direction, for example in an anticlockwise direction. This causes the lancet 309 to be removed from the user's digit, and for the disc edge 305 at the cutaway portion 302 to rub the user's digit as the test disc member 208 rotates. At a point in the rotation of the test disc member 208, the lowermost part of the second guide member 206 ceases to coincide with the cutaway portion 302 and so is able to exert a reaction force on the upper surface 303 of the test disc member 208. A short time thereafter, the lowermost part of the first guide member 205 becomes coincident with the cutaway portion 302, and ceases to contact the upper surface 303 of the test disc member 208. At this point, it is the second guide member 206 that prevents the first test disc member 208 moving upwards within the cartridge 206.

The test disc member 208 continues to rotate until the blood collection portion 315 is aligned with the aperture 105. Here, rotation ceases. At this location, blood that has been caused to be expelled from the user's digit by the lancet 309 and by action of the disc edge 305 on the user's digit is caused to be drawn to the analyte measuring part 316 by capillary action. The blood and the enzyme then react.

At a suitable time, the shaft 204 is caused to be rotated further in the opposite direction, for example in an anticlockwise direction. Here, the test disc member 208 is caused to be rotated from the position shown in FIG. 10, in which the blood collection portion 315 is coincident with the aperture 105, to the position shown in FIG. 11. Here, the notch 301 is aligned with the second guide member 206. Because at this location the first guide member 205 is coincident with the cutaway portion 302 of the test disc member 208, neither of the first or second guide members 205, 206 prevents upwards movement of the first test disc member 208. As such, the first to third disc members 208 to 210 are moved upwards by virtue of the bias means (not shown).

Figure 11:
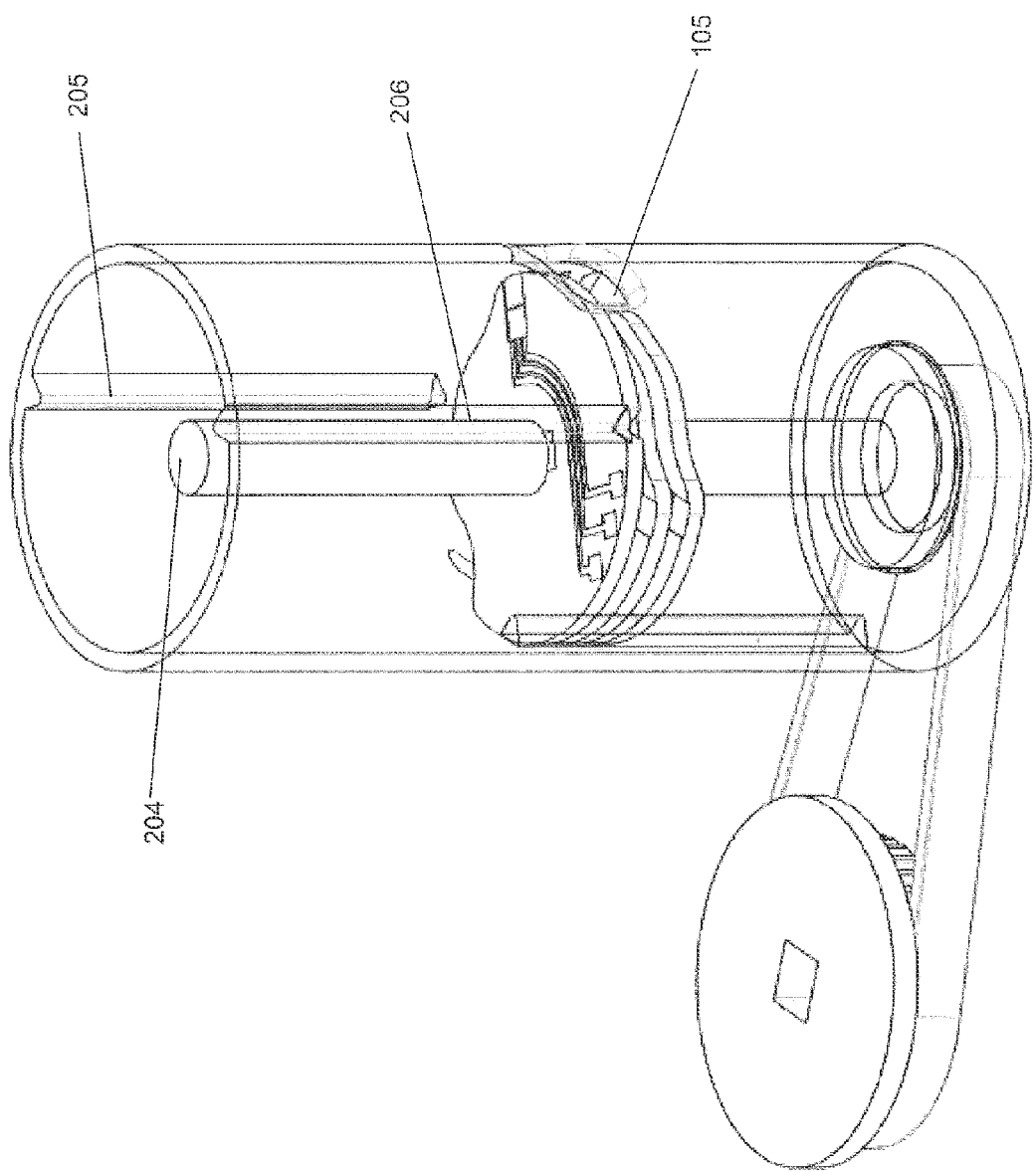
Figure 12:
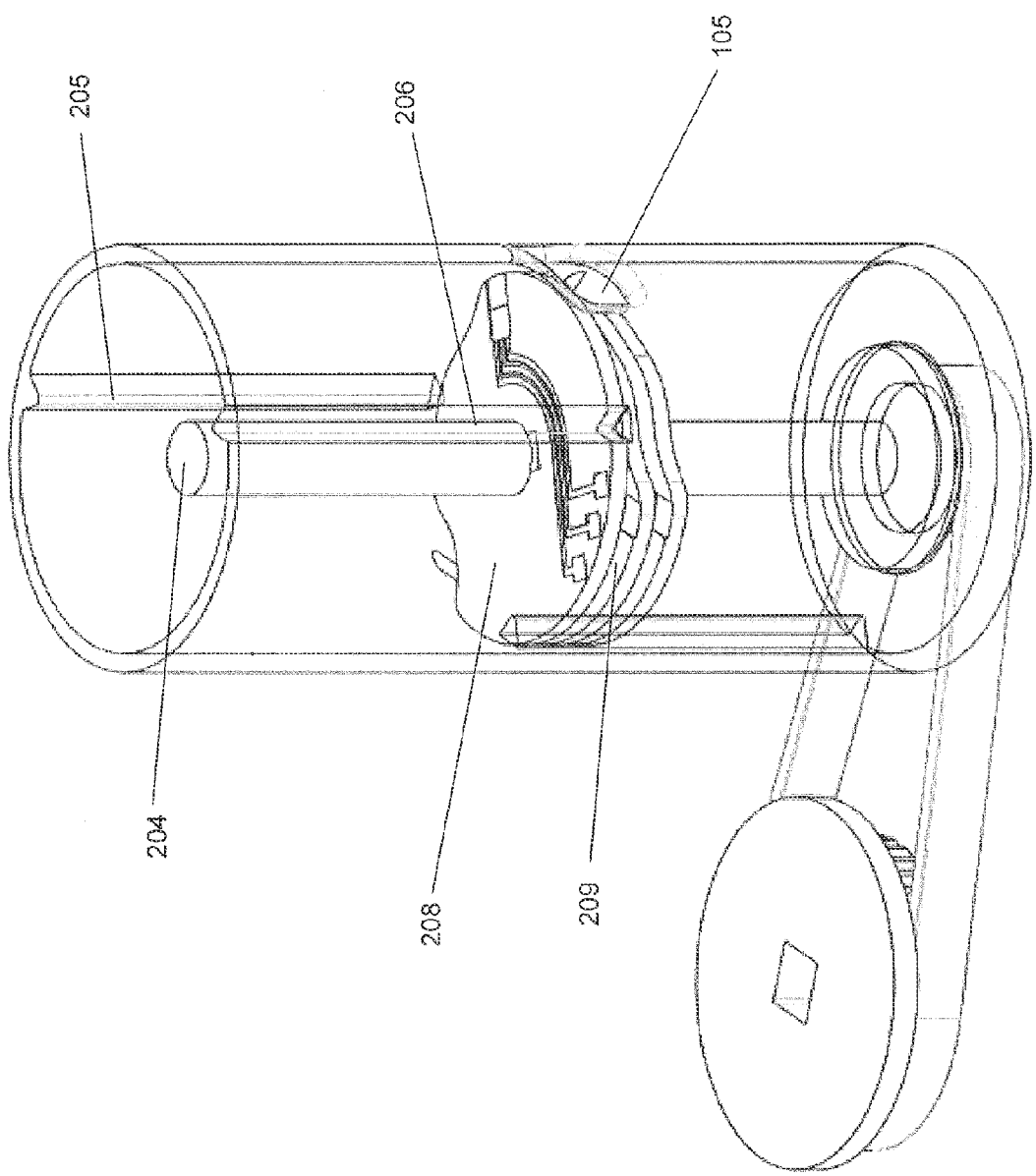

When the first test disc member 208 moves upwards, between FIGS. 11 and 12, the drive dog 320 ceases to cooperate with the drive notch 307 of the hole 306 of the first test disc member 208. Before the first test disc member 208 reaches the position shown in FIG. 12, a lower surface of the drive dog 320 contacts the upper surface 303 of the second test disc member 209. This prevents further upward movement of the second test disc member 209, and thus prevents further movement of the test disc member 210. At this position, the shaft 204 is caused to be rotated by the drive wheel 201 and the drive belt 202 such that the drive dog 320 is coincident with the drive notch 307 of the second test disc member 209. At this location, the second disc member 209 is able to move upwards on the shaft 204, thereby engaging the drive dog 320 with the drive notch 307 of the second test disc member 209. After the second test disc member 209 has moved upward by a distance equal to the height of the spacer member 308, further upwards movement of the second test disc member 209 is prevented by contact between the first guide member 205 and the upper surface 303 of the second test disc member 209. At this point, which is shown in FIG. 12, the second guide member 206 is located within the notch 301 of the first test disc member 208. This prevents further rotation of the first test disc member 208 within the cartridge 106.

By virtue of movement up the cartridge 106 of the first to third test disc members 208 to 210, the third guide member 207 ceases to be within the notch 301 of the second test disc member 209. At this stage, the third guide member 207 does not prevent rotational movement of the second disc member 209.

At the position shown in FIG. 12, the second test disc member 209 is in exactly the same position as was the first test disc member 208 at the position shown in FIG. 6. Furthermore, the shaft 204, and thus the drive dog 320, has the same orientation. As such, the second test disc member 209 is able to be used to elicit a blood sample from a user and test the glucose level thereof in the same way as was the first test disc member 208.

By providing a stack of test disc members 208 to 210 within the cartridge 106 and by providing a suitable physical arrangement, a cartridge 106 can be used for multiple tests. When the cartridge 106 is new, the test disc members 208 to 210 are located in the bottom half of the cartridge 106, with the uppermost test disc member being aligned with the aperture 105. As test disc members are used, the stack of test disc members moves upwards in the cartridge. When the last test disc member is used, the cartridge can be said to be spent. At this stage, all of the test disc members are located in the uppermost portion of the cartridge 106.

It will be appreciated that the number of test disc members 208 to 210 that can be accommodated within the cartridge 106, and thus the number of tests that can be provided by a cartridge 106, is a factor of the height of the cartridge 106, and the separation between corresponding parts (e.g. the upper surfaces) of adjacent test disc members 208 to 210. A taller cartridge and/or a reduced separation of test disc members increases the number of tests that can be performed using a single cartridge 106.

Referring now to FIGS. 13 to 18, an arrangement in accordance with aspects of the invention is shown. Here, the arrangement and operation is as described above with reference to FIGS. 5 to 12 unless otherwise stated. Reference numerals are retained from earlier described figures for like elements.

Figure 13:
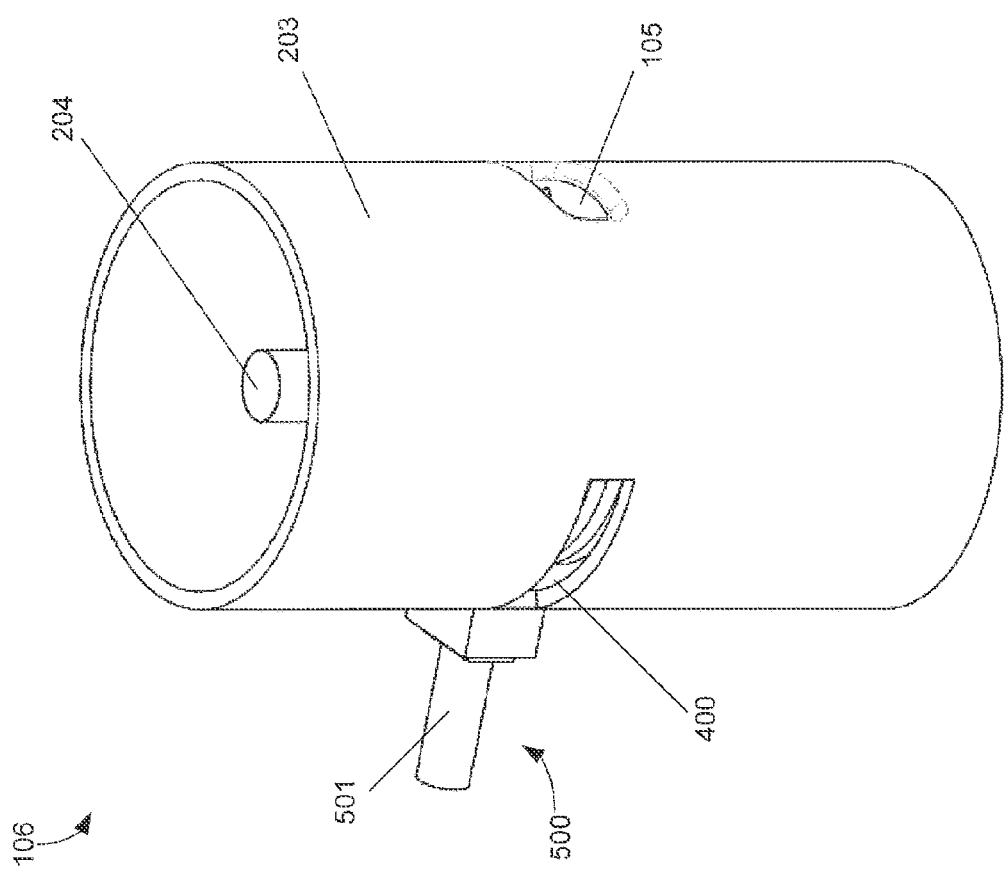
FIG. 13 illustrates components of BGM of FIG. 1 embodying aspects of the invention in a perspective view.

As shown in FIG. 13, the hollow cylindrical housing part 203 is provided with the aperture 105 and the slit aperture 400. The shaft 204 is supported centrally within the hollow cylindrical housing part 203 of the cartridge 106. However, the diameter of the shaft is less than in FIGS. 5 to 12.

A plunger arrangement 500 comprising a plunging arm 501 and a plunging head 502 is provided adjacent a plunging aperture (not shown) in the hollow cylindrical housing part 203. The plunging aperture (not shown) is located next to the slit aperture 400. The plunging aperture (not shown) is located directly opposite to the aperture 105. The plunger aperture and the slit aperture 400 may be combined to form a single aperture. The plunger aperture is configured to allow the plunging head 502 to be forced by the plunging arm 501 to a position internal to the hollow cylindrical housing part 203.

Figure 14:
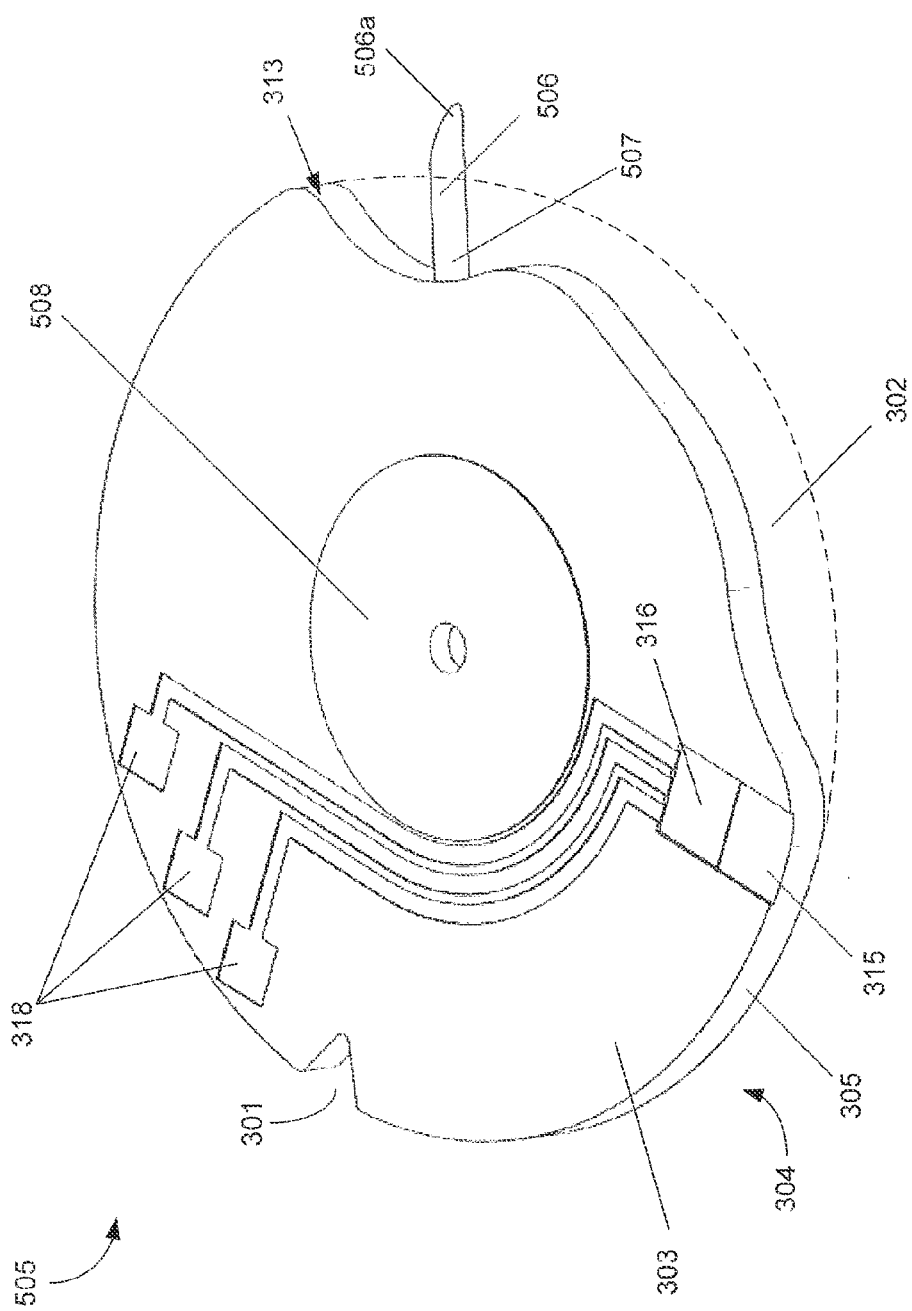
FIG. 14 illustrates a test disc member forming part of the FIG. 13 embodiment.

Within the cartridge 106 are plural test disc members, one of which is shown as 505 in FIG. 14.

A lancet 506 is provided extending from the disc edge 305 in the cutaway portion 302. In particular, the lancet 506 extends in a radial direction with respect to the centre of the test disc member 505. The lancet 506 extends from a fourth position 507, which is near to the second position 313. The fourth position 507 is further from the second position 313 than is the corresponding first position 312 in the arrangement described above with reference to FIGS. 5 to 12. However, because the lancet 506 is radial with respect to test disc member 505, a distal end 506A of the lancet 506, i.e. the end that is furthest from the centre of the test disc member 505, is at approximately the same position as the corresponding end of the lancet 309.

The majority of the test disc member 505 is substantially rigid. However, an annular centre portion 508 is comprised of an elastically deformable material. In particular, the annular centre position 508 is deformable in the presence of an externally applied force. This means that the test disc member 505 can be displaced relative to the shaft 204, as will be described in more detail below. The material used to form the annular centre portion 508 may take any suitable form, and for instance may be a rubberised plastic.

Figure 15:
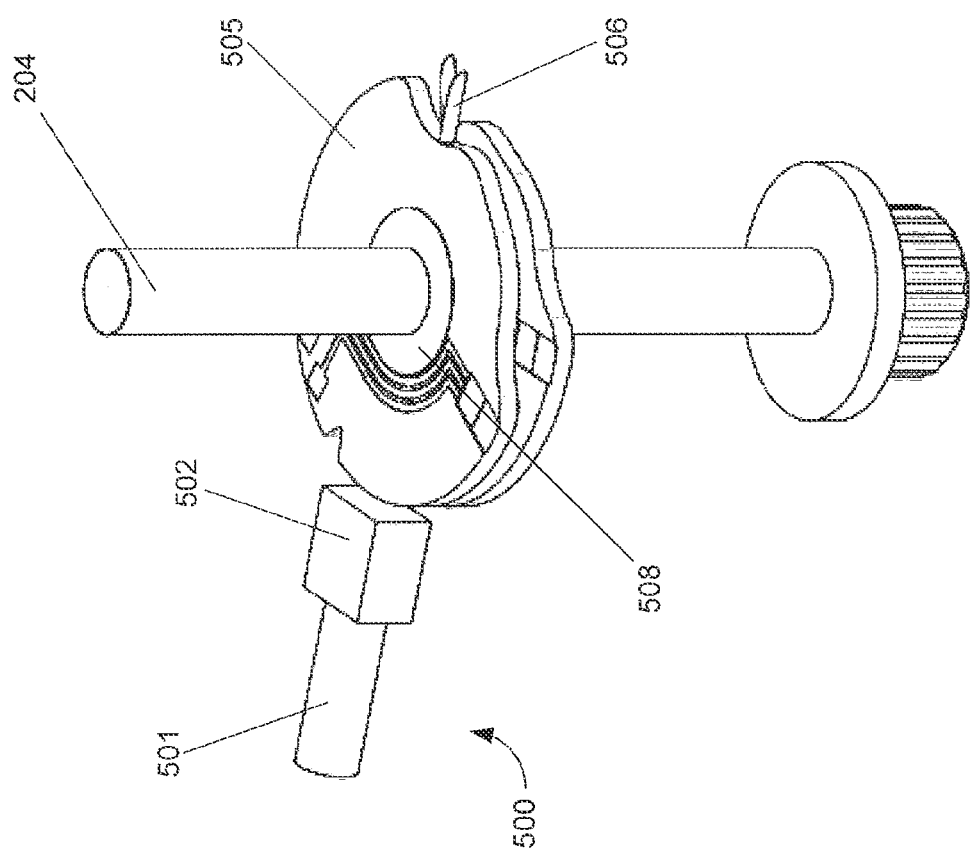
FIGS. 15 to 18 illustrate the embodiment of the BGM of FIG. 13 at different phases of operation.

In FIG. 15, the hollow cylindrical housing part 203 is omitted from the figure. In FIG. 15, the test disc member 505 is shown as having been rotated to a position at which the lancet 506 is coincident with the aperture 105. It can be seen that the plunging head 502 is aligned with the test disc member 505 such that movement of the plunger arrangement 500 along the longitudinal axis of the plunging arm 501 causes the plunging head to contact the test disc member 505 and apply force to it. Since the longitudinal axis of the plunging arm 501 is radial with respect to the shaft 204, the force applied by the plunger arrangement is directed towards the shaft 204.

Figure 16:
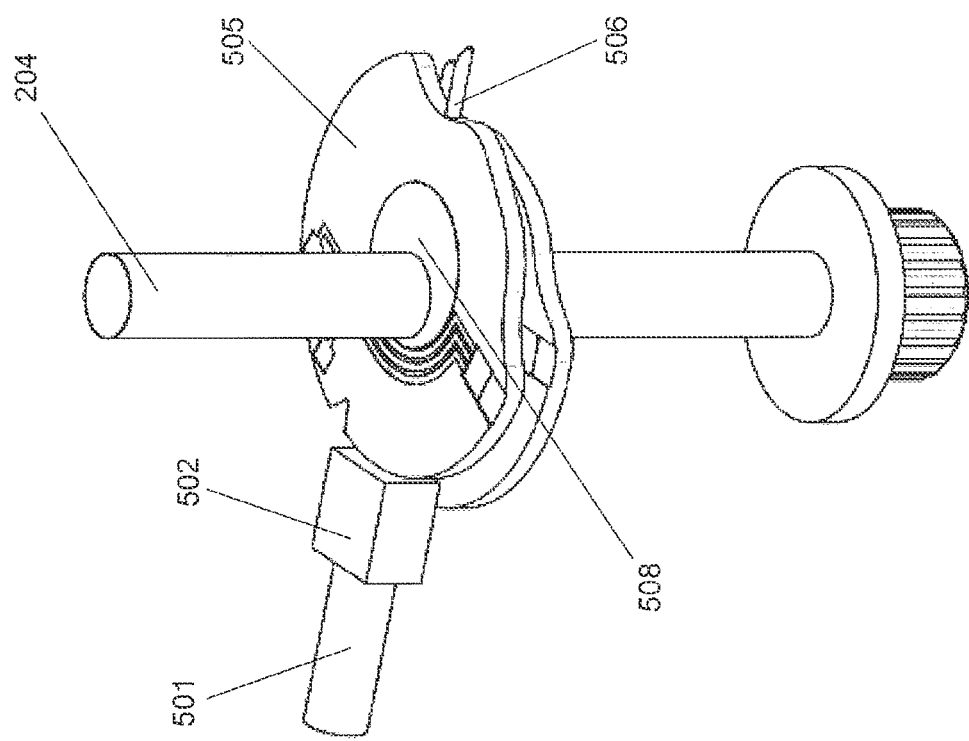

In FIG. 16, the arrangement is shown after a force has been applied to the plunger arrangement 500 so as to displace it by a predetermined amount. Here, the plunging head 502 has contacted the test disc member 505 on the opposite side of the test disc member to the lancet 506. The annular centre portion 508 has become compressed on the side closest to the plunger arrangement 500 such as to allow the whole of the test disc member 505 to be displaced in the direction of the force supplied by the plunger arrangement 500. The test disc member 505 remains horizontal by virtue of the spacer members 308.

Displacement of the test disc member 505 in the direction of the force supplied by the plunger arrangement 500 has resulted in displacement of the lancet 506 in a radial direction away from the shaft 204. In this position, the lancet 506 penetrates the skin of the user's digit. Removal of the force by the plunger arrangement 500 allows the annular centre portion 508 to return to its original form, through elastic reformation. After the plunger arrangement 500 has been fully retracted, the arrangement again has the form shown in FIG. 15. Here, the test disc member 505 is in its original position and the lancet 506 is retracted from the user's digit. It will be appreciated that it is the elasticity of the annular centre portion 508 of the test disc member 505 that allows the test disc member 505 to return to this position once the force applied through the plunger arrangement 500 is removed.

Figure 17:
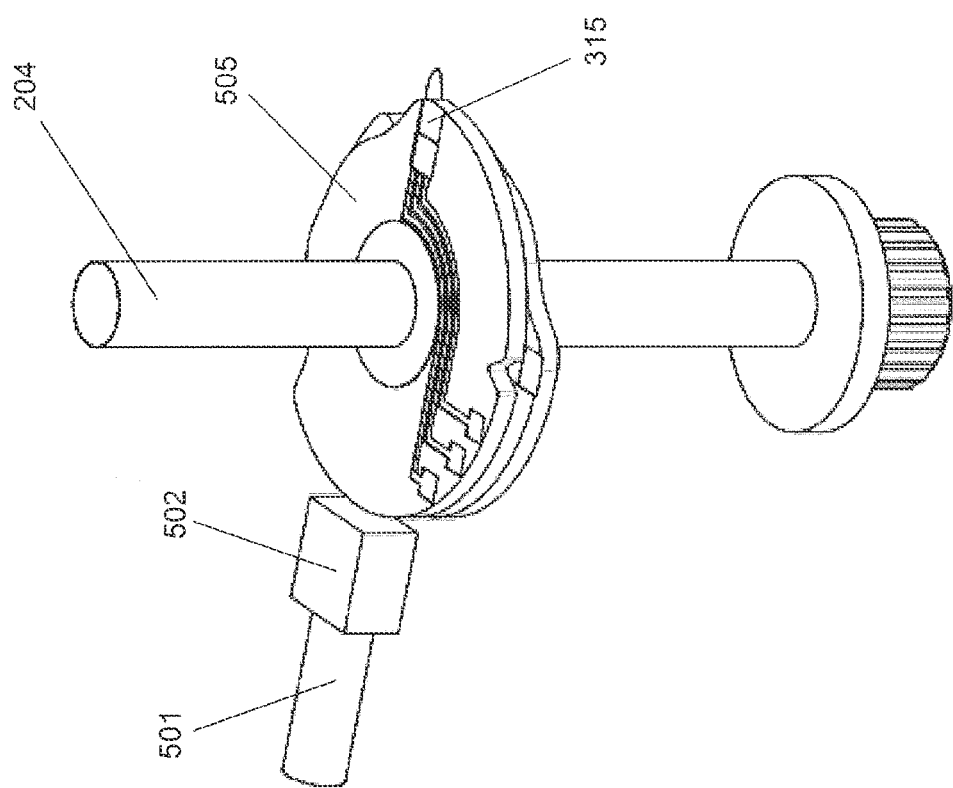
Figure 18:
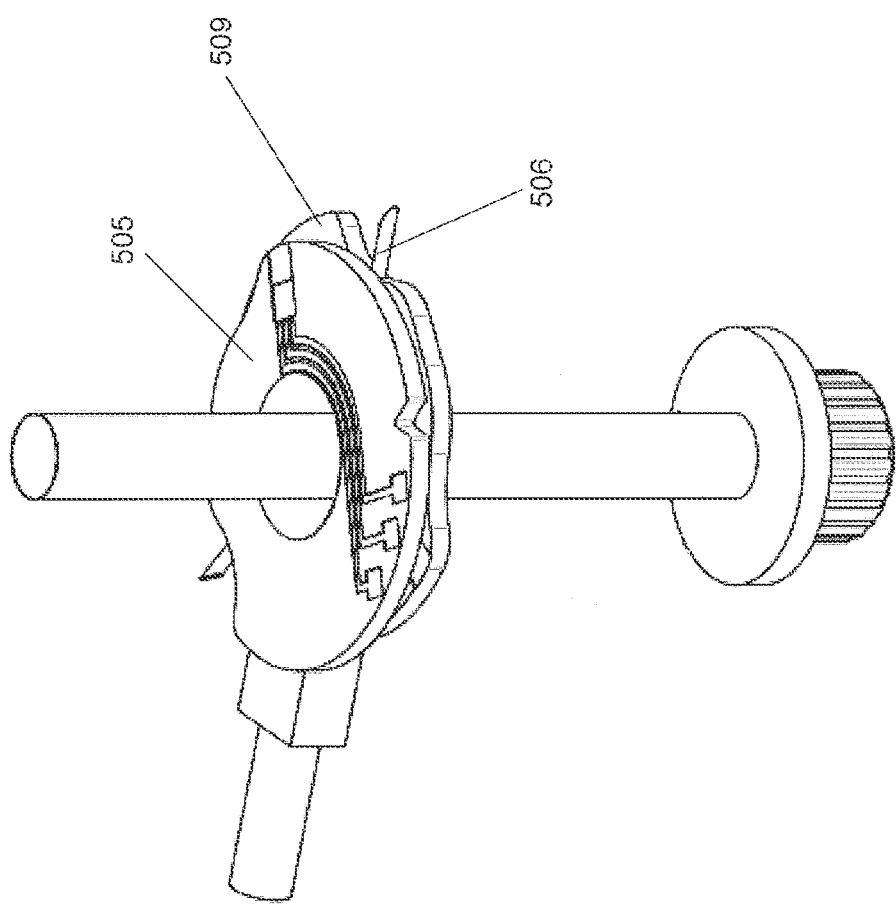

After removal of the force supplied by the plunger arrangement 500, the test disc member 505 can be rotated by the drive wheel 201 and the drive belt 202 so as to provide milking of the user's digit and then collection of blood at the blood collection portion 315, which position is shown in FIG. 17. After a measurement of blood glucose level is taken, the test disc member 505 is rotated further anticlockwise so that the second guide member 206 is aligned with the notch 301, and thus the test disc member 505 is allowed to move upwards within the cartridge 106. As a result, the test disc member 509 that is immediately below the first test disc member 505 also moves upwards within the cartridge 106 and is provided to be coincident with the aperture 105, the slit aperture 400 and the plunger aperture (not shown). Subsequent application of a plunging force by the plunger arrangement 500 causes a lancet 506 of the second test disc member 509 to be forced out of the aperture 105, as is shown in FIG. 18. The process can be repeated for other test disc members included in the cartridge 106.

An advantage of the arrangement shown in FIGS. 13 to 18 is that a rotational arrangement can be used whilst allowing the lancet 506 to penetrate a user's skin in a longitudinal direction with respect to the lancet 506. Another advantage is that puncture can occur at any desired location, for instance on the end of the user's digit, instead of puncturing occurring slightly on the side of the end of the digit.

Another advantage is that the arrangement can allow the penetration depth of the lancet 506 to be easily predictable.

Furthermore, it allows the penetration or puncturing depth to be adjustable. In particular, the adjustment of the penetration depth can be achieved by a mechanical arrangement that limits movement of the plunger arrangement towards the shaft 204. Alternatively, it can be achieved in an electro-mechanical manner by measuring the location or displacement of some part of the mechanism and ceasing applying an energising voltage to a solenoid or other transducer that is used to affect movement of the plunger arrangement 500. The penetration depth may be specified by a user. The depth may be specified by a user may be achieved through software or firmware control of rotation of the shaft 204. The penetration depth may be defined by the user for example using one or more of the first, second and third inputs 101 to 103. For instance, the first and second inputs 101, 102 may be increase and decrease respectively, with the third input 103 being a select or confirm input. The value defining the depth may be stored in memory. Penetration depth control is important to many users since lancet penetration usually is painful and since penetration depth control allows users some control over their experience.

Figure 19:
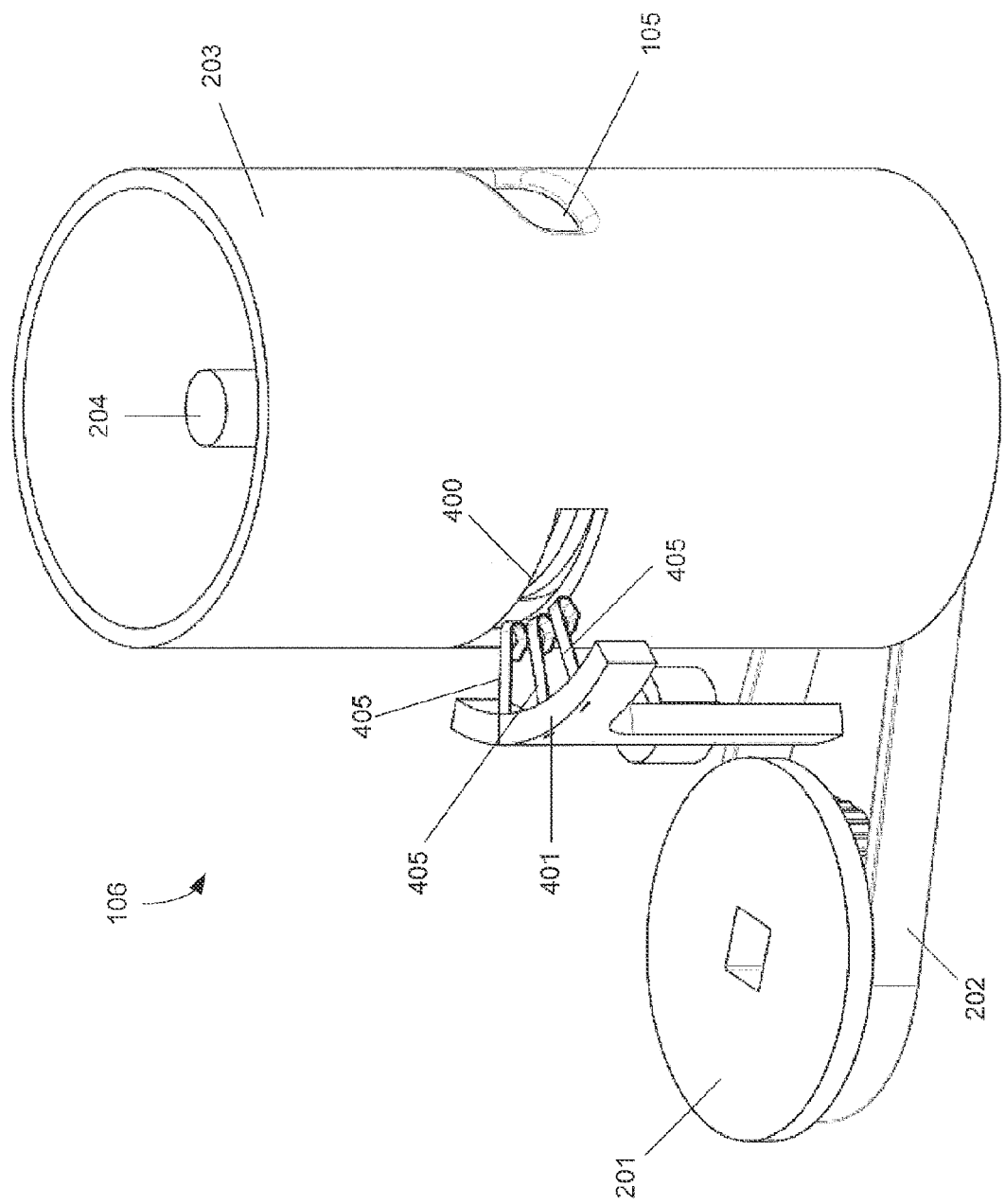
FIG. 19 is a perspective view of components of the BGM of FIG. 1.
Figure 20:
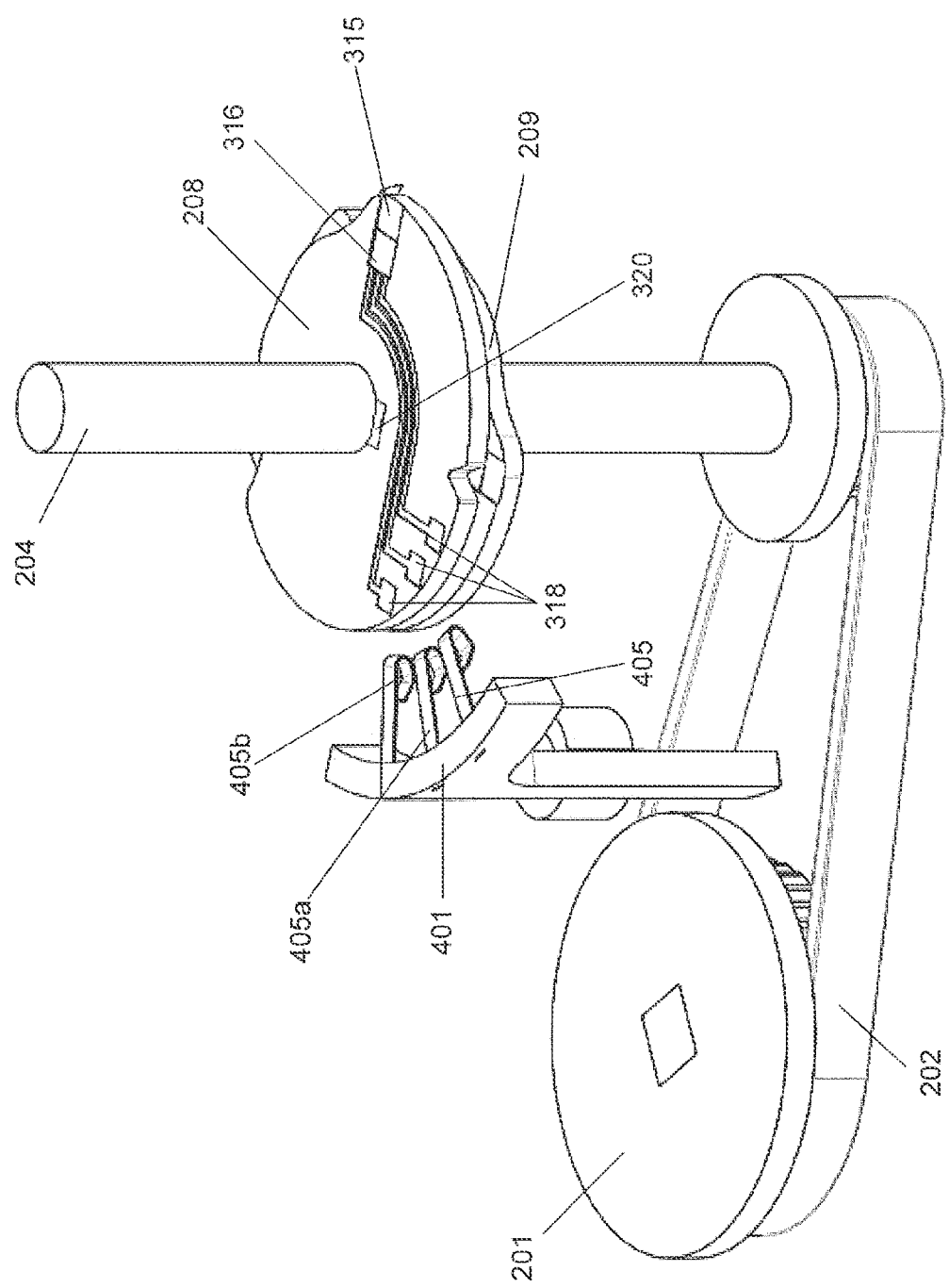
FIG. 20 is the same as FIG. 19, although with a hollow cylindrical housing part not shown.
Figure 21:
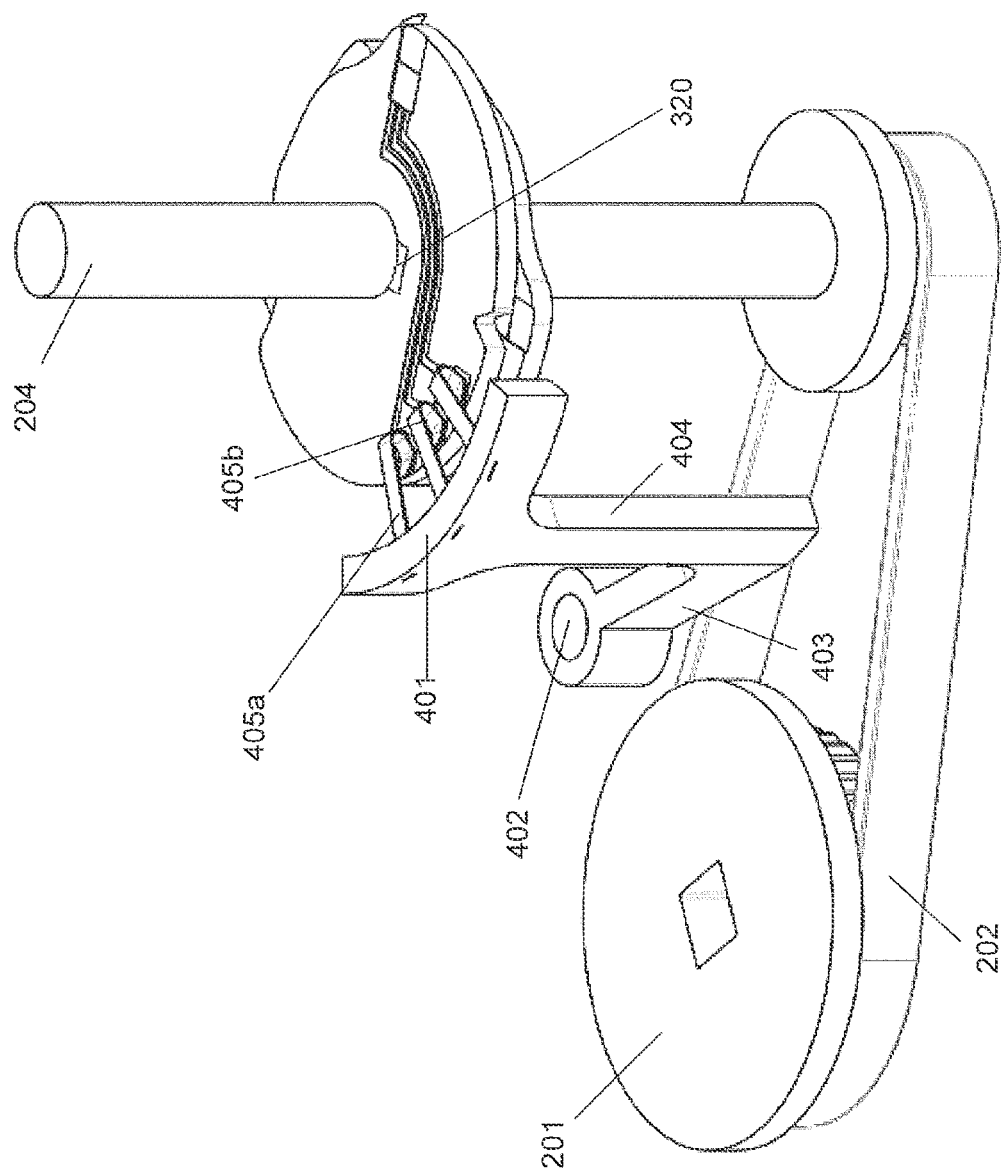
FIG. 21 is the same as FIG. 20 although with a swing arm located in a different position.

Reference will now be made to FIGS. 19 to 21, which illustrate connection of the analyte measuring part 316 to measurement circuitry (not shown).

Referring firstly to FIG. 19, the hollow cylindrical housing part 203 is shown with the aperture 105 and the shaft 204 located as described above. A slit aperture 400 is provided in the hollow cylindrical housing part 203. The slit aperture 400 is located at substantially the same height as the aperture 105. However, the slit aperture 400 is located on a side of the hollow cylindrical housing part 203 that is substantially opposite the aperture 105.

The slit aperture 400 does not coincide with the elongate aperture 110 that is formed at the front side of the BGM 100. As such, the slit aperture 400 is not visible when the cartridge 106 is in place within the BGM 100.

FIG. 20 is the same view as shown in FIG. 19 although the hollow cylindrical housing part 203 is omitted.

Adjacent to the slit aperture 400 is located a swing arm 401. The swing arm 401 is rotatable about a spindle 402, as shown in FIG. 21. The spindle 402 has an axis that is parallel to the axis of the shaft 204. The axis of the spindle 402 is located above the drive belt 202. A connecting arm 403 connects the spindle 402 to the swing arm 401. In this example, the connecting arm 403 is connected to the swing arm 401 by a vertical connector 404. The vertical connector 404 allows the spindle 402 on which the connecting arm 403 is mounted to be located at a different vertical position to the swing arm 401. The spindle 402, the connecting arm 403 and the vertical connector 404 are arranged such that when the connecting arm is rotated on the axis of the spindle 402 the swing arm 401 is moved towards the shaft. The movement of the swing arm 401 is substantially radial with respect to the shaft 204.

Mounted on the swing arm 401 are first to third electrical contact terminals 405. Each includes a generally horizontal arm 405a and a depending contact head 405b. The electrical contact terminals 405 are made of a resilient conductive material, for instance metal. The depending contact heads 405b are angled at their ends furthest from the swing arm 401.

In one position, shown in FIGS. 19 and 20, the electrical contact terminals 405 are supported by the swing arm 401 such that the dependent contact heads 405b are located within the slit aperture 400 or alternatively outside of the hollow cylindrical housing part 203. When the test disc member 505 is rotated such that the blood collection part 315 is coincident with the aperture 105, as shown in FIG. 20, the contact pads 318 are coincident/aligned with the slit aperture 400. As the test disc member 505 is held in this position, the connecting arm 403 is caused to rotate around the axis of the spindle 402 such that the swing arm 401 moves towards the shaft 204. The arrangement is such that the depending contact heads 405b of the electrical contact terminals 405, but not the horizontal arms 405a, come into contact with the contact pads 318 as the electrical contact terminals 405 move into the volume above the upper surface 303 of the test disc member 505. The resilient properties of the electrical contact terminals 405 causes the electrical contact terminals to be forced against the contact pads 318. As such, an electrical connection is provided between the horizontal arms 405a of the electrical contact terminals 405 and the analyte measuring part 316. Electronic measuring means (not shown) connected to the electrical contact terminals 405 operate to pass a voltage through the contact terminals 405 and the analyte measuring part 316 and to take measurements of electrical parameters, from which a measurement of an analyte concentration level, for example a blood glucose level, can be determined.

The connecting arm 403 is controlled to remain in a position shown in FIG. 21 for a predetermined time or alternatively until it is detected that a blood glucose level measurement has been made, after which the connecting arm 403 is caused to rotate around the shaft 402 so as to remove the electrical contact terminals 405 from the position above the upper surface of the test disc member 505. At this stage, the arrangement is as shown in FIG. 20. Once the electrical contact terminals 405 have been retracted, the test disc member 505 is rotated anticlockwise so as to allow the test disc members 505 to move upwards on the shaft 204.

It will be appreciated that the maximum permissible height dimension of the electrical contact terminals 405 is determined by the height of the spacer member 308. A thicker spacer member allows larger electrical contact terminals 405 to be used. However, this is at the expense of an increase in separation between adjacent test disc members 505, and thus a reduced capacity for the cartridge 106. The use of electrical contact terminals 405 including a horizontal arm 405a and a depending contact head 405b allows the height dimension of the electrical contact terminals to be minimised whilst allowing good electrical contact between the electrical contact terminals and the contact pads 318 and also allowing the electrical contact terminals 405 to operate correctly over a sufficient number of cycles.

The configuration of the test disc members 505 is such that operation results in milking of the puncture in the user's digit caused by the lancet 506. In particular, the aperture 105 is configured such as to allow an amount of the flesh making up the end of the user's digit to be present within the internal volume of the cylindrical part 203 when the user presses the digit up against the aperture 105. When the user applies force into the aperture 105 with the digit, the digit distorts and a bulbous part is provided within the internal diameter of the hollow cylindrical housing part 203. The size of the bulbous part, and in particular the height of the bulbous part, depends on a number of factors, including the physical characteristics of the user's digit and the amount of force that the user applies, as well as the configuration of the aperture 105.

The aperture 105 is dimensioned such that in normal use (i.e. with a typical user applying a typical amount of force) a bulbous part of the user's digit extends into the internal volume of the hollow cylindrical housing part 203 to a depth of approximately 1 millimeter. The test disc members 505 are configured to have a cutaway portion 302 that is shaped such that when the lancet 506 is at a position at which it can lance the user's digit, the disc edge 305 is not in contact with the user's digit (i.e. the separation between the disc edge 305 and the aperture 105 is greater than 1 mm). This part of the cutaway portion 302 can be termed a first milking portion. At this position, the pressure exerted by the user results in the fluid pressure within the bulbous part of their digit being slightly greater than normal pressure. The increased pressure results from the force the user applies to their digit. This pressure encourages bleeding of the puncture that is caused by the lancet 506. Advantageously, the arrangement of the relevant features is such that the lancet 506 penetrates the user's digit to a depth of between 0.4 and 0.7 millimeters.

As the test disc member 505 rotates anticlockwise after lancing, the end of the bulbous part of the user's digit comes into contact with the disc edge 305 at a position approximately one-third to two-fifths of the way along the cut out portion 203. This part can be termed the second milking portion. The test disc member 208 to 210, 505, 600 has a substantially constant radius for the second milking portion, which extends to a position approximately two-thirds or four-fifths of the way along the cutaway portion 302. For the time at which the second milking portion is coincident with the bulbous part of the user's digit as the test disc member 208 to 210, 505 rotates, the internal pressure of the bulbous part of the user's digit is increased compared to the time at which the user's digit was in contact with the lancet 309. Furthermore, as the disc edge 305 moves into contact with and over the bulbous part of the digit, blood under the skin is caused to be pushed towards the puncture caused by the lancet.

Between the second milking part and the location of the blood collection part 315, the radius of the test disc member 505 is reduced, or put another way has a lower value. This portion can be termed a third milking portion. As such, after the second milking portion and before the user's digit contacts the blood collection part 315, the pressure applied to the bulbous part of the user's digit by the disc edge 305 is reduced compared to the pressure applied at the second milking portion. Advantageously, the radius of the test disc member 505 at the third milking portion is selected such that the bulbous part of the user's digit does not contact the disc edge 305 (i.e. the separation between the disc edge 305 and the aperture 105 is greater than 1 mm). Whilst the third milking portion is coincident with the user's digit as the test disc member 505 rotates, blood is free to exit the puncture made by the lancet 506. As the test disc member 505 continues to rotate, the disc edge 305 again contacts the bulbous part of the user's digit at a location just before the blood collection portion 315. This again increases the internal pressure within the bulbous part of the user's digit. This encourages the movement of blood towards the analyte measuring part 316. The separation between the disc edge 305 at the location of the blood collection portion 315 and the aperture 105 is approximately 0.5 mm.

The configuration of the test disc members 505 thus encourages milking of a sample of blood from the user's digit. The sequence is as follows: Firstly, lancing by the lancet 506 with a relatively low pressure (caused by no contact with the disc edge 305 and the user's digit), followed by a period for which relatively low amount of pressure, as well as a rubbing movement, is provided by the second milking portion to the user's digit, followed by a period for which little or no pressure is provided by the disc edge 305 against the user's digit, followed by a relatively high pressure provided by the disc edge 305 against the user's digit just before and at the blood collection part 315.

Figure 22:
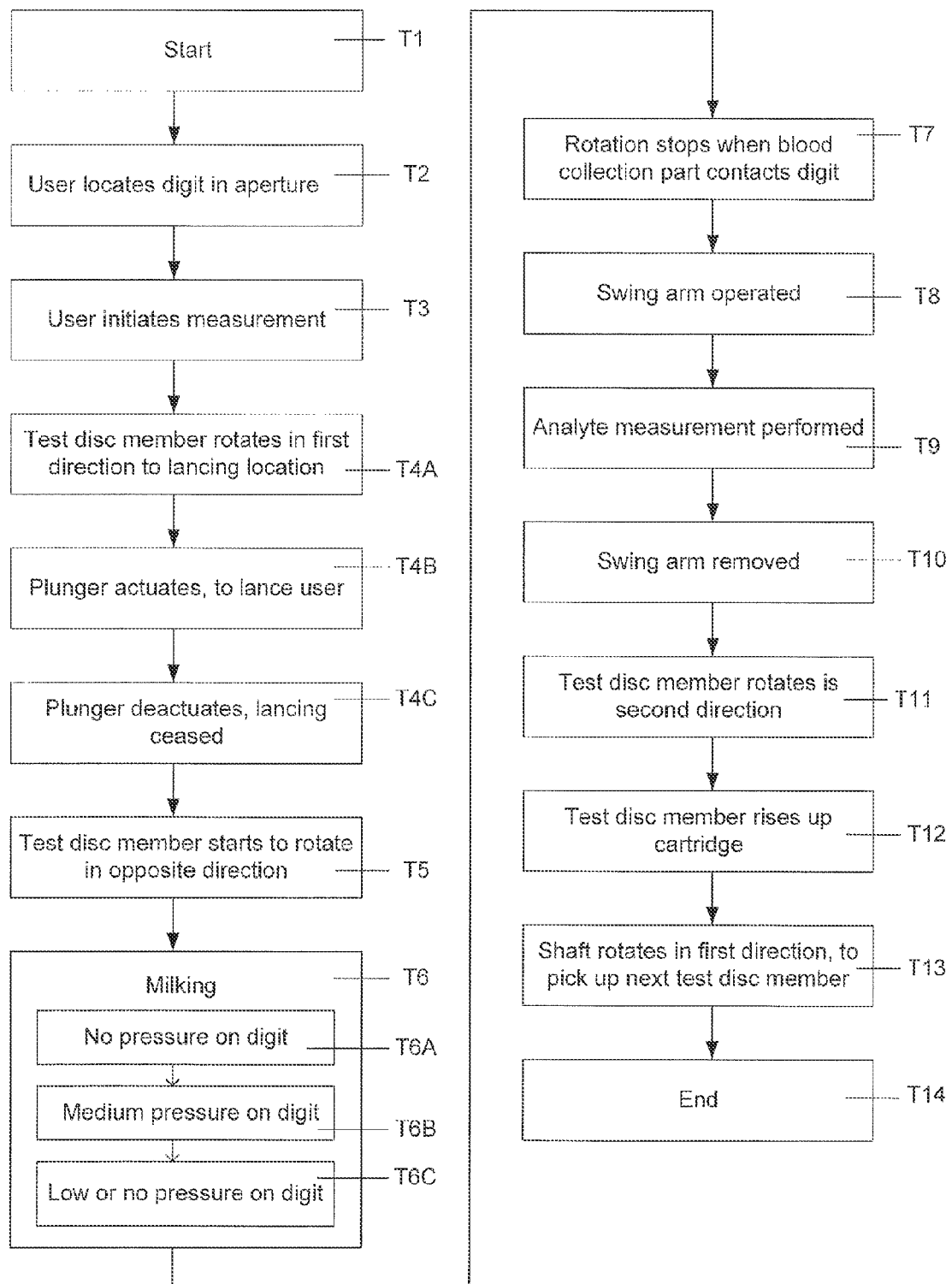
FIG. 22 is a flowchart illustrating operation of the BGM of FIG. 1.

Operation of the blood glucose meter 100 will now be described with reference to the flowchart of FIG. 22.

Operation starts at step T1. At step T2, the user locates their digit in the aperture 105. As mentioned above, the user forces their digit into the aperture 105 with a pressure or force that is suitable to allow lancing and blood collection. At step T3, the user initiates blood glucose measurement. This involves the user pressing one of the inputs 101 to 103. This is detected by the microprocessor 212 by way of the keys interface 215. The software/firmware stored in the ROM 214 uses the key input to call a function or to execute a software module. The software/firmware stored in the ROM 214 then causes the microprocessor 212 to issue a command to a motor attached to the drive wheel 201 through the motor interface 217 to rotate the shaft 204 in a first direction, for example in a clockwise direction. The software/firmware controls the extent of the rotation.

Following step T3, the microprocessor 212, under control of the software/firmware stored in the ROM 214, causes the shaft 204 to be rotated by a motor through the motor interface 217 and to cease rotation once the lancet 508 is aligned with the aperture 105, and thus is aligned with the user's digit, at step T4A. At step T4B, the microprocessor 212, under control of the software/firmware stored in the ROM 214, causes actuation of the plunger arrangement 500, through the motor interface 217. The control of the actuation of the plunger is such as to limit the extent of movement of the lancet 508 to a predetermined extent. The predetermined extent is set by a user through operation of the keys 102, 103 prior to the blood glucose measurement. In effect, the user can use the keys 102, 103 to set a lancing depth, which is stored in a suitable way in the ROM 214 by action of the microprocessor 212, operating under control of the software/firmware stored in the ROM 214.

When the maximum extent of plunger actuation has been reached at step T4B, at step T4C the plunger arrangement 500 is deactuated by the microprocessor 212, under control of the software/firmware stored in the ROM 214, and lancing ceases. At this step, the test disc member returns to its original position by action of the elasticity of the annular centre portion 508 of the test disc member 508.

Although in the figures, an in particular in FIG. 7, three conductive tracks 317 and three conductive pads 318 are shown, it will be appreciated that this is merely illustrative. There may instead be only two conductive tracks 317 and two conductive pads 318, or alternatively there may be more than three conductive tracks and conductive pads.

The software/firmware stored in the ROM 214 then causes the microprocessor 212 to control the motor to rotate the shaft 204 in the opposite direction, at step T5. As the test disc member rotates anticlockwise, milking occurs at step T6. Firstly, at step T6A, there is no pressure applied by the test disc member on the digit. At step T6B, there is a medium amount of pressure on the digit. At step T6C, there is low or no pressure applied by the test disc member on the digit. At this point, the digit coincides with the part of the test disc member that is immediately before the blood collection part 315.

At step T7, the software/firmware causes the microprocessor 212 to control the motor to cease rotation when the shaft 214 is such that the blood collection member 315 is coincident with the aperture 105, and thus the user's digit. At step T8, the software/firmware controls a motor such as to cause the swing arm 401 to be rotated towards the shaft 204. The software/firmware stored in the ROM 214 is such that the microprocessor 212 causes only the required amount of travel of the swing arm 401. At this point, the analyte interface circuit 219 is coupled directly to the blood analyte measuring part 316, which by action of the blood collection part 315 has been provided with blood from the user's digit. At step T9, analyte measurement is performed. This involves the analyte interface circuit 219 providing voltages to the electrical connection contacts 318, and thus to the blood analyte measuring part 316, and measuring parameters of resulting signals. The measured parameters, particularly voltage parameters, are used by the software/firmware stored in the ROM 214, as executed by the processor 212, to calculate a blood glucose measurement level of the user. The blood glucose measurement is then caused by the software/firmware to be displayed on the display 104 through action of the microprocessor 212 on the display drive 216. At step T10, the swing arm is caused to be removed by action of the microprocessor 212, under control of the software stored in the ROM 214, the motor interface 217 and the motor (not shown).

At step T11, the software/firmware results in the microprocessor 212 controlling the drive disc 201 to rotate in the opposite direction. Rotation continues until the notch 301 on the test disc member is coincident with the guide 206. At step T12, the test disc member rises up the cartridge 106. In the case where biasing of the test discs up the cartridge 106 is provided by a bias means, for instance a spring, step T12 requires no action on part of the software/firmware and microprocessor 212, although there may be a pause before the next step. In embodiments where movement of the test disc members along the shaft 204 occurs through driving action, step T12 involves the microprocessor 212, under control of the software/firmware stored in the ROM 214, controlling a motor through the motor interface 217. Subsequently, at step T13, the microprocessor 212, under control of the software/firmware stored in the ROM 214, causes the shaft 204 to rotate again in the first direction and to cease rotating when the drive dog 320 engages with the drive slot 307 of the next test disc member in the cartridge 106. At this stage, the test disc members rise up the cartridge 106 slightly.

The operation ends at step T14.

Various modifications and alternative features can be used in connection with the above-described embodiments. Some alternatives now follow.

Instead of the blood collection part 315 being located next to the third position 314, i.e. bounding only the part of the disc edge 305 that is purely circumferential, the blood collection part could instead be located on the disc edge 305 at the junction between the cutaway portion 302 and the circumferential portion. The blood collection 315 part in this instance may extend for between 0.5 mm and 2 mm along the disc edge 305 at the cutaway portion 302. The blood collection 315 part in this instance may also extend for between 0.5 mm and 2 mm along the disc edge 305 at the circumferential part.

Alternatively or additionally, the analyte measuring part 316 may be sandwiched between two layers of wicking material, the wicking material causing the blood to be drawn through the analyte measuring part 316.

Although in the above the shaft 204 is said to be driven by a drive wheel 201 that is coupled to the shaft 204 by a drive belt 202, the drive may instead be direct (i.e. the drive mechanism is coupled directly to the shaft 204), or connection may be made by a notched belt, a vee belt, or by a direct gear mechanism. Instead of an electric motor, a clockwork drive could be used. A clockwork drive mechanism has a number of advantages, particularly where access to batteries or battery chargers or electricity supplies are limited. In the embodiments in which a clockwork mechanism is used, the user can be sure that the BGM 100 will not cease operating because of drained batteries. A clockwork mechanism may be particularly suited to developing countries and emerging markets.

In embodiments in which an electrical motor is used to drive the shaft 204, preferably control is exerted over the motor by software. In this way, the speed of rotation can easily be controlled. Additionally, the extent of rotation can more easily be controlled. The motor may be a stepper motor.

Alternatively, a mechanical drive arrangement may be present, for instance using a lever or other device for manual actuation. A suitable mechanism may be one similar to those previously used in SLR cameras.

The swing arm 401 may be actuated in any suitable way. For instance, it may be driven by the same motor or mechanism as the shaft 204. Alternatively, it may be driven by a separate motor. In either case, the rotation of the swing arm 404 may be affected by a cam mechanism, or by a pin and slot (track path) mechanism. In the event of an electric motor being used, the motor preferably is software driven. The motor preferably is a stepper motor.

The mechanical arrangement may include a mechanism by which a bias means, for instance a mechanical compression spring, is biased and then released in order to push the electrical contact terminals 405 into place. The terminals 405 can then be refracted by the swing arm 401 using a rotating motion. The overall mechanism can be termed a latch type trigger mechanism.

Instead of a swing arm 401 being used to rotate the electrical contact terminals 405 into place, the contact pads 318 may instead be located on the disc edge 305, allowing the use of fixed electrical contact terminals 405. The electrical contact terminals may include a brush or other deformable feature such that the test disc members 208 to 210, 505, 600 can move whilst in contact with the electrical contact terminals without damage occurring to any of the components. Similar arrangements are used in brushed DC motors. In this case the electrical contact terminals 405 could be flexible finger contacts that rest on the periphery of the test disc members 208 to 210, 505, 600 in order to contact the contact pads 318.

Alternatively, instead of a swing arm 401, a mechanism may be used to affect longitudinal movement of the electrical contact terminals 405 into place to contact the contact pads 318.

The conductive tracks 317 and the contact pads 318 may be formed by leadframe. Alternatively, overmoulding may be used. Alternatively, printed circuit board (PCB) printing may be used.

Optionally, each of the test disc members 209, 210, 505, 600 is separated from adjacent test disc members by a membrane (not shown in the drawings). In this case, the membrane preferably fits closely to the internal surface of the hollow cylindrical housing part 203. An effect of the membrane is to reduce the possibility of disc cross-contamination. Use of a membrane may allow the test disc members 208 to 210, 505, 600 to have a reduced separation than would be the case without the use of a membrane.

In the above, the test disc members 505 are said to be biased upwards by a bias means, for instance a compression spring. Alternative mechanisms for moving the test disc members 505 up the cartridge may be used. For instance, a threaded lifting cam may be provided on the shaft 204 or alternatively on the interior surface of the hollow cylindrical housing part 203. Alternatively, the test disc members 505 may remain stationary, with the aperture 105 and the drive dog 320 instead being moved along the axis of the cartridge 106. Movement of the aperture 105 may be achieved by the use of a sliding door in an elongated slot. Movement of the door allows a different strip to be revealed at the aperture 105.

Instead of the blood collection portion 315 wicking blood towards the analyte measuring part 316, blood may be communicated to the analyte measuring part 316 instead through gravity.

Additionally, the test disc members 505 may include a disinfecting or cleaning portion that contacts the digit before lancing. This can reduce risk of infection of the wound and also can increase accuracy in particular by removing any glucose from the skin (as may occur after eating fruit etc.).

Additionally or alternatively, the test disc members 505 may include a cleaning portion that is arranged to contact the digit subsequent to the blood collection part 305. This can remove additional blood from the finger, and may also serve to assist closure of the puncture.

The invention claimed is:

1. Apparatus for eliciting a blood sample, the apparatus comprising:
   a housing having an aperture;
   a shaft mounted inside the housing;
   a testing member rotatably mounted on the shaft;
   an actuating member coupled to the housing and configured to exert a force against the testing member; and
   a lancet fixedly coupled to and protruding substantially radially from the testing member and configured to co-rotate with the testing member;

wherein the apparatus is configured such that the lancet is aligned with the aperture in the housing when the testing member is in a first position, and wherein the testing member is configured, in the presence of a force exerted against the testing member by the actuator member, to translate to a second position in which the lancet is in a skin penetrating position.

2. Apparatus according to claim 1, comprising an elastic member associated with the member and/or the shaft and configured to allow the testing member to translate into the second position in the presence of the force exerted against the testing member by the actuating member.

3. Apparatus according to claim 2, wherein the elastic member comprises at least part of a first annulus that surrounds a core of the shaft.

4. Apparatus according to claim 3, wherein the first annulus is configured to be compressed on the side between an inner core and the testing member, thereby facilitating the translation of the testing member, in the presence of the radial force between the testing member and the housing.

5. Apparatus according to claim 1 wherein apparatus is configured such that the testing member returns to the first position when the force is released.

6. Apparatus according to claim 1 wherein the testing member further comprises a blood sample collection part and a blood analyte measuring part.

7. Apparatus according to claim 6 wherein when the testing member is in a third position the blood collection part is aligned with the aperture.

8. Apparatus according to claim 7 wherein the apparatus is further configured such that the testing member is configured to translate from the third position to a fourth position in the presence of a radial force against the testing member.

9. Apparatus according to claim 8, wherein in the fourth position the blood collection part is in a user contacting position.

10. Apparatus according to claim 1, wherein the actuating member is a plunger supported by the housing and configured to exert the radial force against the testing member.

11. Apparatus according to claim 1, wherein the testing member further comprises at least two electrical contact points connected to the blood collection part for communication with a meter.

12. Apparatus according to claim 11 wherein the meter is a blood glucose meter.

* * * * *